United States Patent [19]

Bert et al.

[11] Patent Number: 5,234,433
[45] Date of Patent: Aug. 10, 1993

[54] METHOD AND INSTRUMENTATION FOR UNICOMPARTMENTAL TOTAL KNEE ARTHROPLASTY

[75] Inventors: Jack M. Bert, Woodbury, Minn.; Richard W. Woods, Baltimore, Md.

[73] Assignee: Kirschner Medical Corporation, Timonium, Md.

[21] Appl. No.: 779,525

[22] Filed: Oct. 18, 1991

Related U.S. Application Data

[62] Division of Ser. No. 412,318, Sep. 26, 1989, Pat. No. 5,122,144.

[51] Int. Cl.$^5$ .............................................. A61B 17/56
[52] U.S. Cl. .................................... 606/88; 606/96; 606/102
[58] Field of Search ................. 606/79, 80, 82, 84, 606/86-88, 96, 102; 623/16, 18, 20, 22, 23

[56] References Cited

U.S. PATENT DOCUMENTS

| | | |
|---|---|---|
| 4,457,307 | 6/1984 | Stillwell . |
| 4,467,801 | 8/1984 | Whiteside . |
| 4,470,158 | 9/1984 | Pappas et al. . |
| 4,474,177 | 10/1984 | Whiteside . |
| 4,567,885 | 2/1986 | Androphy . |
| 4,574,794 | 3/1986 | Cooke et al. ............ 606/88 |
| 4,703,751 | 11/1987 | Pohl . |
| 4,719,908 | 1/1988 | Averill . |
| 4,736,737 | 4/1988 | Fargie et al. . |
| 4,759,350 | 7/1988 | Dunn et al. . |

FOREIGN PATENT DOCUMENTS 0243109 10/1987 European Pat. Off. .............. 606/87

OTHER PUBLICATIONS

Copy of brochure entitled "Current, Leading Technology Has Finally Been Applied to a Unicompartmental Knee System", Zimmer, Inc., Warsaw, Ind.
Brochure entitled "Principles and Techniques of Unicompartmental Knee Arthroplasty", Johnson & Johnson Orthopaedics, copyright 1987.
Brochure entitled "The PCA(TM) Unicompartmental Knee System", Howmedica, copryight 1985.
Brochure entitled "Unicompartmental Knee System, OMNIFIT(R) from Osteonics", copyright 1986.
Brochure entitled "Whiteside ORTHOLOC(R) II, Unicondylar Knee Systems", Dow Corning Wright, copyright 1988.

Primary Examiner—Randall L. Green
Assistant Examiner—D. Willse
Attorney, Agent, or Firm—Frost & Jacobs

[57] ABSTRACT

A method and instruments for replacing the articulating surfaces of a knee joint in which the diseased area is restricted to one of the medial and lateral compartments. A femoral intramedullary rod is placed down the center of the femur. A femoral cutting block is affixed at one side to the rod and at the other side to an outrigger attached to the femur by smooth pins. The cutting block is adjustable rotationally and in the anterior-posterior plane. The cutting block is provided with surgical saw guide slots for the posterior and distal articular surface cuts and the chamfer cuts, all of which are made with the cutting block in place. The cutting block is removed and a drill guide is used for drilling two holes in the distal articular cut surface for receipt of the mounting pegs of the femoral unicompartmental prosthetic implant. A tibial intramedullary rod is placed down the center of the tibia, to which is adjustably affixed a vertical cutting block, a horizontal cutting guide and a caliper measuring device. The caliper measuring device is used to properly locate the cutting guide and the horizontal tibial cut is made. Upon removal of the measuring device and cutting guide, the cutting block is used to guide the vertical cut. The cutting block and tibial intramedullary rod are removed. The tibial prosthesis is comprises a tray and a snap-in bearing insert. A tibial template is placed on the horizontal tibial cut surface and a hole for the tray mounting peg is drilled together with additional holes for mounting screws, if used.

18 Claims, 15 Drawing Sheets

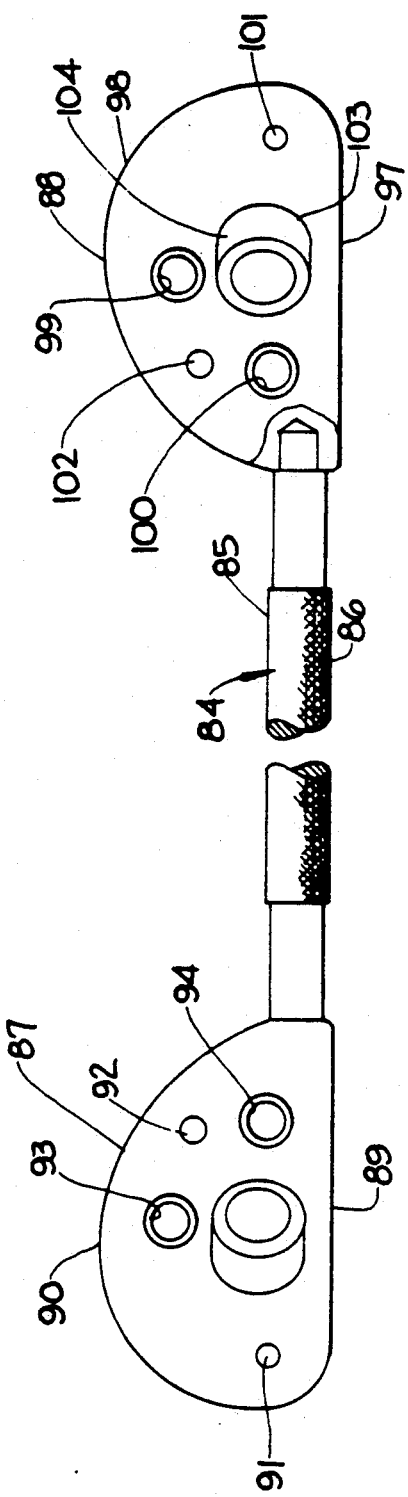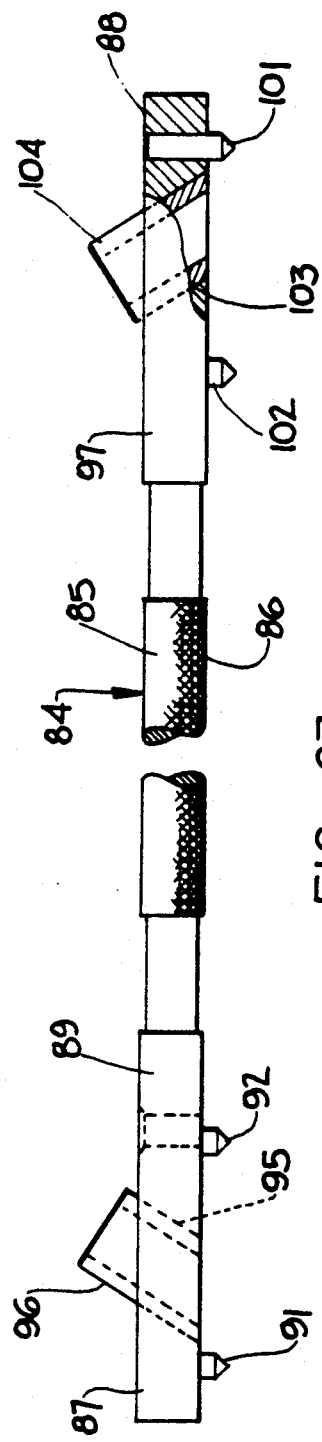
FIG. 26
FIG. 27

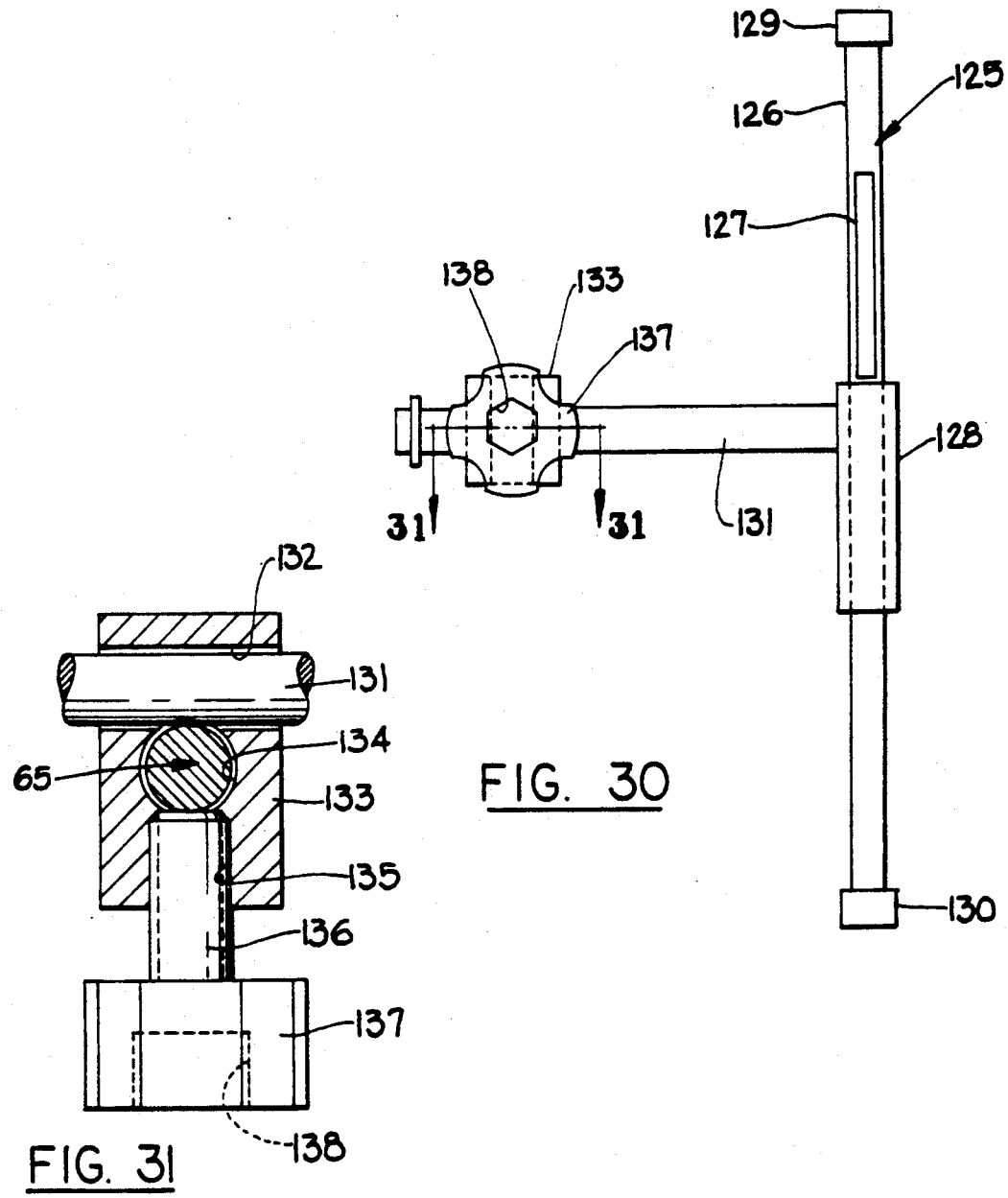

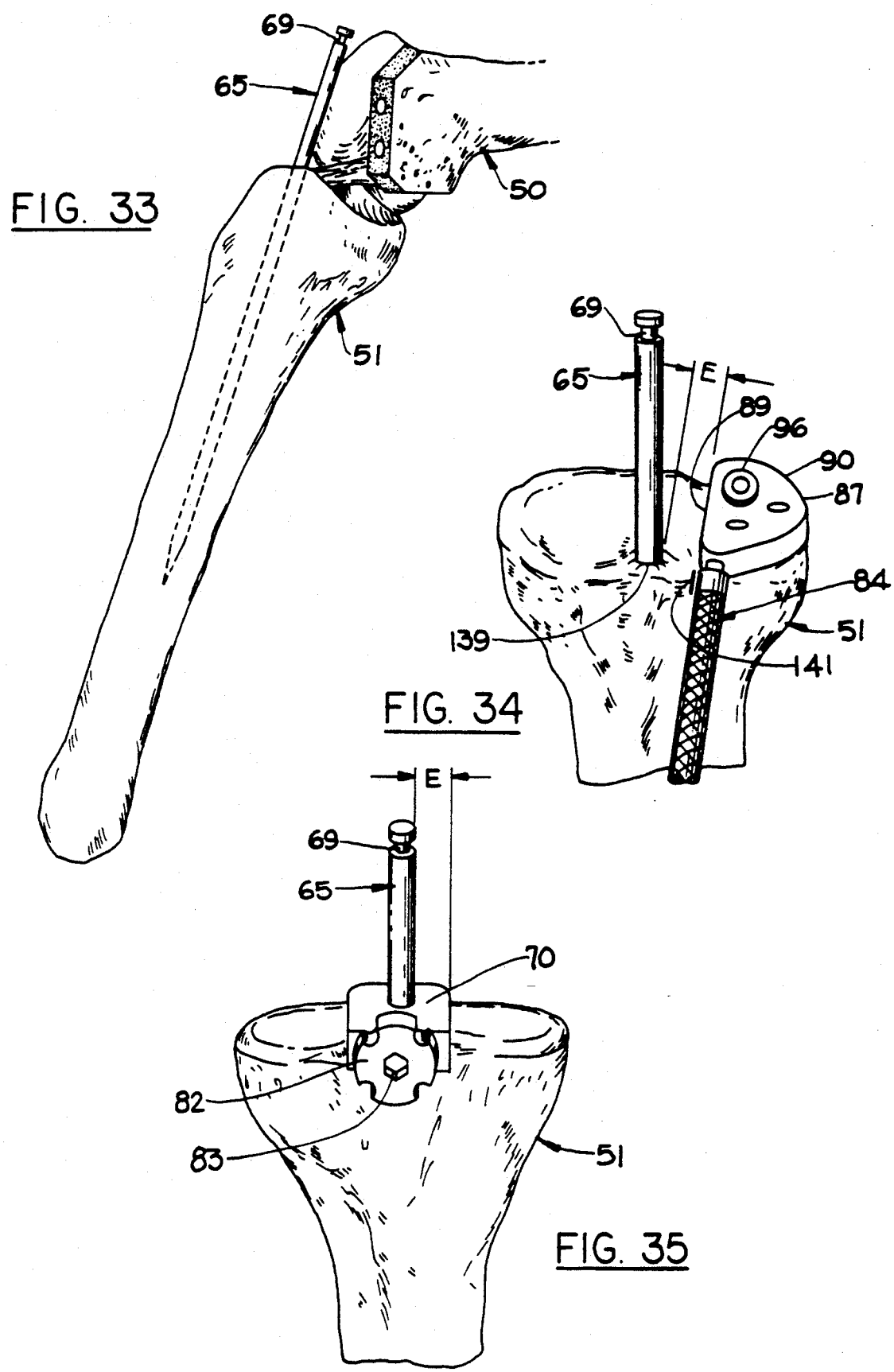

METHOD AND INSTRUMENTATION FOR UNICOMPARTMENTAL TOTAL KNEE ARTHROPLASTY

This is a divisional of application Ser. No. 07/412,318, filed Sep. 26, 1989, Now U.S. Pat. No. 5,122,144.

TECHNICAL FIELD

The invention relates to unicompartmental total knee arthroplasty, and more particularly to an improved method and improved instrumentation therefor.

BACKGROUND ART

The present invention is directed to the replacement of the articulating surfaces of a knee joint in which the diseased area is restricted to either the medial or the lateral compartment, not both, and which still maintains good ligamentous stability. As compared to tricompartmental total knee arthroplasty, unicompartmental total knee arthroplasty, when its use is indicated, has a number of advantages. These advantages include less hospitalization, decreased blood loss, increased range of motion, and decreased pain.

Prior art workers have devised a number of procedures in unicompartmental total knee arthroplasty. The accuracy and reproducibility of the associated femoral and tibial cuts for preparation of the femur and tibia to receive their respective prostheses has long been a major concern to the orthopaedic surgeon Prior art procedures and instruments require the serial fixation, removal and replacement of numerous cutting blocks to prepare the bone, basing secondary cuts on the not-so-inherent accuracy of the initial cuts.

The present invention is based upon the development of a method and instrumentation which allow the surgeon to complete all of the femoral and tibial cuts with one guide assembly for each. Both the femoral and the tibial guide assemblies are firmly affixed and are left intact until all the cuts have been completed, while still maintaining the versatility required for proper positioning.

The surgical procedure followed for preparing the distal femur bases the cuts on the affected condyle only, and does not disturb the unaffected side in any manner. Fixation of the single femoral cutting guide block is achieved utilizing the diseased side only.

The method and instrumentation of the Present invention enables the use of a conventional femoral prosthesis having a pair of mounting pegs and a tibial prosthesis which comprises a tibial tray having anteriorly and posteriorly placed locking lips which engage the flexible tabs on the corresponding sides of a removable plastic bearing insert. The bearing insert is available in multiple thicknesses and both the tray and the insert are provided in left and right configurations. The tibial tray includes a rigidly affixed, posteriorly angled peg. According to the present invention, the tray also includes a medial and an anterior hole for screws by which it may be additionally affixed to the tibia. The posteriorly angled peg in conjunction with the screws provides divergent forces on the tibia to keep the tray firmly fixed. The femoral and tibial prostheses may also be affixed by an appropriate bone adhesive. The holes in the tibial tray for the mounting screws may be plugged with plastic inserts, when the mounting screws are not used.

In the preparation of the distal femur, a single cutting block is used. The cutting block is adjustable in the anterior-posterior plane and rotationally, and is firmly affixed to the femur by a femoral intramedullary rod on one side of the cutting block and an outrigger assembly on the other side of the cutting block, which is attached directly to the femur by a pair of smooth pins. The cutting block is provided with surgical saw guide slots for the posterior articular surface cut, the distal articular surface cut, and the chamfer cuts. All of these cuts are made with the single cutting block mounted in place. These four cuts can be made in any order. The cutting block can be used for resection of either the medial condylar surface or the lateral condylar surface by reversing the positions of the femoral intramedullary rod and the outrigger.

The surgical procedure followed for preparing the proximal tibia utilizes an intramedullary rod to which all components of the tibial cutting guide assembly are adjustably affixed. The tibial guide assembly includes a horizontal cutting guide which can be rotated about the intramedullary rod and shifted in all radial directions to facilitate proper positioning thereof against the anterior tibial surface on the operative side. The tibial guide assembly also includes a caliper measuring device to assist in the location of the horizontal cutting guide.

The tibial cutting guide assembly additionally includes a vertical cutting block, available in various widths, to guide the surgical saw during the vertical tibial cut.

The tibial cutting guide assembly for making both tibial plateau cuts can be used regardless of component sizing and with either compartment.

DISCLOSURE OF THE INVENTION

According to the invention there is provided both a method and instrumentation for replacing the articulating surfaces of a knee joint in which the diseased area is restricted to either the medial or the lateral compartment. The method employs a conventional femoral unicompartmental prosthetic metallic implant having a pair of mounting pegs and a modular type tibial unicompartmental prosthetic implant available in left and right configurations and comprising a metallic tray having a posteriorly angled mounting peg and a removable plastic bearing insert available in multiple thicknesses and left and right configurations.

A femoral intramedullary rod is placed down the center of the femur. A femoral cutting block is affixed at one of its sides to the femoral intramedullary rod and at the other of its sides to an outrigger which, in turn, is attached to the femur by a pair of smooth pins. The attachment of the femoral cutting block to the femoral intramedullary rod and the outrigger is such as to permit adjustment rotationally and in the anterior-posterior plane and firm fixation in the finally adjusted position. The cutting block is provided with surgical saw guide slots for the posterior and distal articular surface cuts and for the chamfer cuts. All four cuts are made with the cutting block in place.

After the femoral cuts are made, the femoral cutting block is removed and a drill guide is used for drilling two holes in the distal articular cut surface for the receipt of the mounting pegs of the femoral unicompartmental prosthetic implant.

A tibial intramedullary rod is placed down the center of the tibial canal onto which is mounted a tibial cutting guide assembly. The tibial cutting guide assembly comprises a vertical tibial cutting block, a horizontal tibial cutting guide and a caliper measuring device, all three of which are mounted on the tibial intramedullary rod one, above the other, in the order named. The caliper measuring device is used to properly locate the horizontal tibial cutting guide and the horizontal tibial cut is made. The caliper measuring device and the horizontal tibial cutting guide are thereafter removed from the tibial intramedullary rod, and the vertical tibial cutting block is then used to guide the vertical tibial cut. With both tibial cuts performed, the vertical tibial cutting block and the tibial intramedullary rod are removed from the tibia. A tibial template is placed on the horizontal tibial cut surface and a hole is drilled for the tibial tray mounting peg. The tibial tray is provided with countersunk medial and anterior holes to accommodate mounting screws, if used. The tibial template is provided with guide holes so that pilot holes may be drilled for such screws. Once the tibial tray is mounted on the tibia, an appropriately sized plastic bearing insert is mounted in the tray, with a snap fit.

Both the femoral implant and the tibial tray may be affixed in place by means of their mounting pegs and an appropriate adhesive. When this is done, the tibial tray mounting screws might not be used, their pilot holes not drilled, and the mounting screw holes in the tibial tray filled with plastic plugs.

BRIEF DESCRIPTION OF THE DRAWINGS

FIG. 26 is a fragmentary plan view of the tibial marking/drilling template assembly of the present invention.

FIG. 27 is a side view of the tibial marking/drilling template assembly of FIG. 26.

FIG. 30 is an elevational view of the caliper measuring device of the present invention.

FIG. 31 is a fragmentary cross-sectional view taken along section line 31—31 of FIG. 30.

FIG. 33 is a fragmentary perspective view illustrating the placement of the tibial intramedullary rod.

FIG. 34 is a fragmentary perspective view illustrating the use of the tibial marking/drilling template assembly to determine the size of the vertical tibial cutting block to use.

FIG. 35 is a fragmentary perspective view illustrating the mounting of the tibial vertical cutting block of FIGS. 24 and 25.

DESCRIPTION OF THE PREFERRED EMBODIMENTS

For purposes of clarity, the instruments used in the preparation of the distal femur, and the preparation of the distal femur, will first be described. This will be followed by a description of the instruments used in the preparation of the proximal tibia and the preparation of the proximal tibia, itself. In all of the figures, like parts have been given like index numerals.

Figure 1:
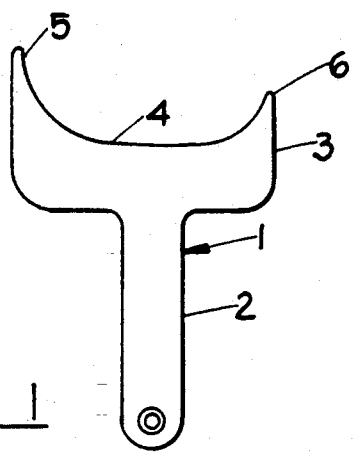
FIG. 1 is an elevational view of the femoral template of the Present invention.
Figure 2:
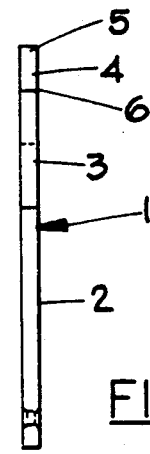
FIG. 2 is an end view of the femoral template as seen from the right of FIG. 1.

FIGS. 1 and 2 illustrate the femoral template of the present invention. The femoral template is generally indicated at 1 and comprises a relatively thin, stainless steel, planar member. The femoral template 1 has a handle portion 2 and a head portion 3. The head 3 has a substantially arcuate measuring surface or edge 4 terminating in posterior and anterior ends 5 and 6, respectively. The template 1 can be used on either the medial or the lateral condyle, of either the left or the right knee. The template 1 is provided in three sizes: small, standard and large.

Figure 4:
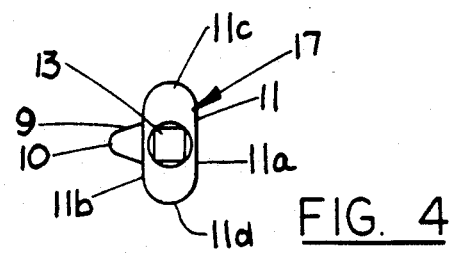
FIG. 4 is a top view of the intramedullary rod of FIG. 3.
Figure 3:
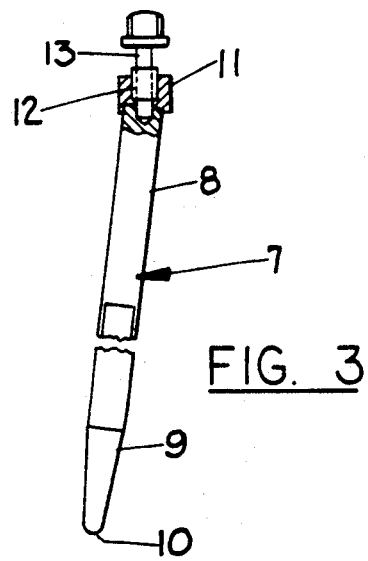
FIG. 3 is an elevational view of the femoral intramedullary rod of the present invention.

The femoral intramedullary rod (hereinafter referred to as the femoral IM rod) is generally indicated at 7 in FIGS. 3 and 4. The femoral IM rod comprises an elongated, rod-like shank 8 having at its lower end a tapered portion 9 terminating in a rounded point 10. At its upper end, there is permanently affixed to the femoral IM rod a head 11 having parallel planar sides 11a and 11b and rounded ends 11c and 11d. The head 11 and the adjacent uppermost end of the femoral IM rod are provided with a threaded bore 12, adapted to receive a bolt 13 provided with a head engageable by a socket wrench. It will be noted that the head 11, the axis of the central bore 12 therein and the axis of bolt 13 are angularly related to the long axis of the shank 8. The femoral IM rod is made in three substantially identical versions, differing only in that the above noted angular relationship is respectively 3°, 5° and 7°. The choice of the appropriate femoral rod to use, will depend upon the valgus orientation of the patient's femoral anatomy. The femoral IM rod assembly, including the bolt 13, is made of stainless steel.

Figure 5:
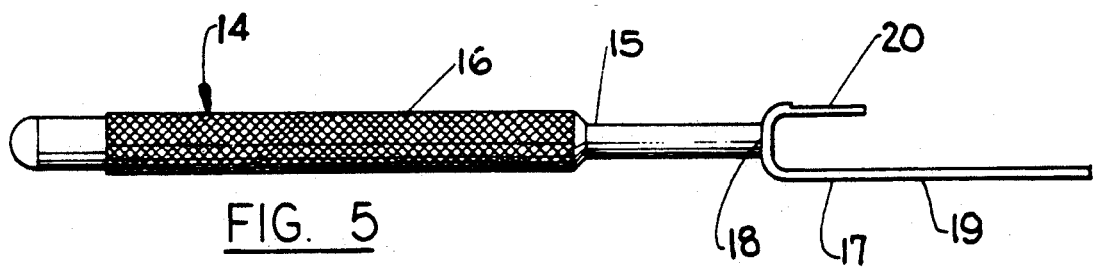
FIG. 5 is a side elevational view of the femoral cutting guide locator of the present invention.
Figure 10:
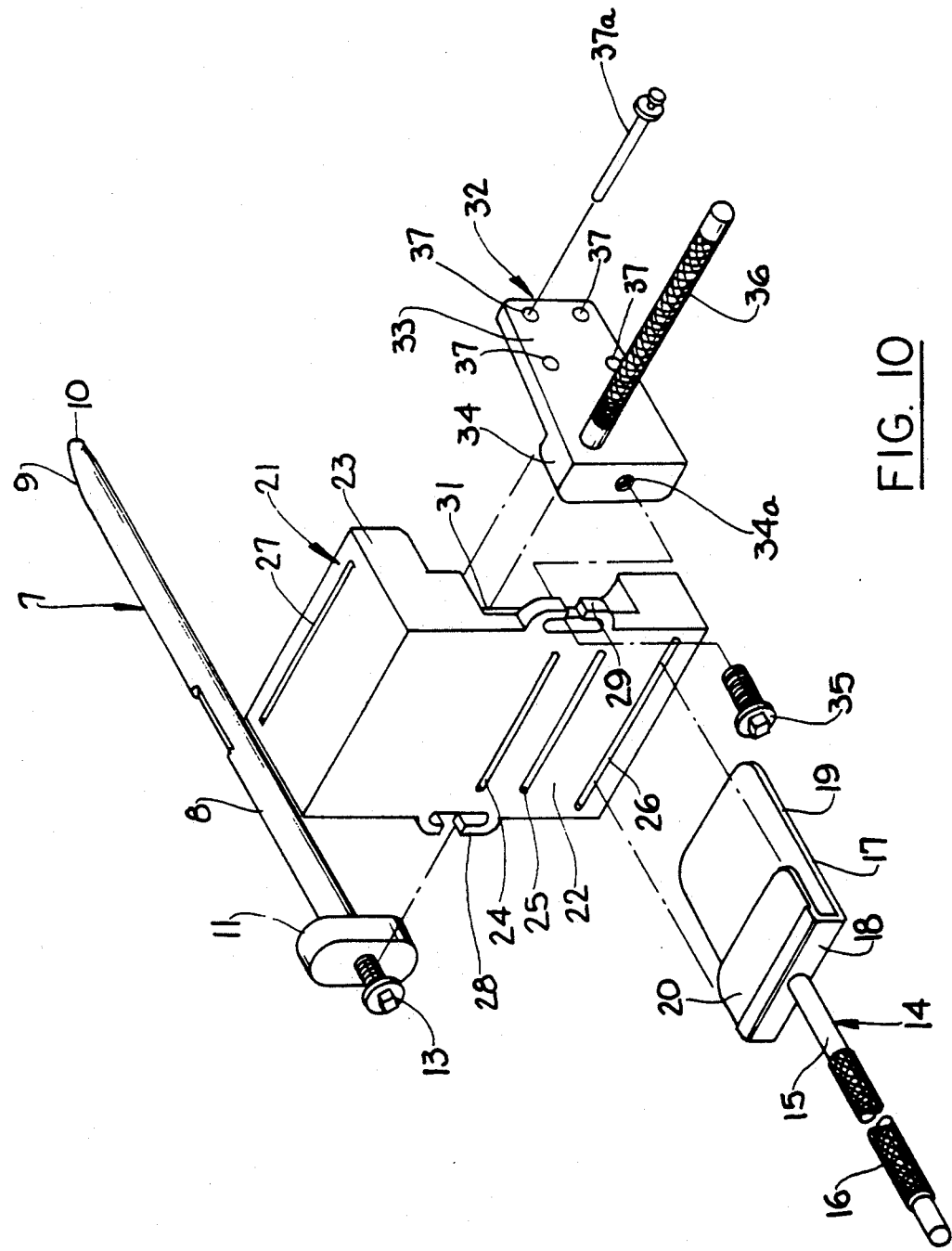
FIG. 10 is an exploded perspective view of the full femoral cutting block assembly of the present invention.

FIGS. 5 and 10 illustrate the femoral cutting block locator, generally indicated at 14. This instrument comprises an elongated handle 15, a portion 16 of which may be knurled to assure a secure grip by the hand of the surgeon. The handle 15 supports at one end a U-shaped member 17 having a base portion 18 terminating in a long leg 19 and a short leg 20. The short leg 20 is slightly thinner than the remainder of the U-shaped member 17 so that it can be received in a posterior cutting slot of the femoral cutting block (see FIG. 10), as will be apparent hereinafter. The femoral cutting guide locator is also made of stainless steel.

Figures 6, 7:
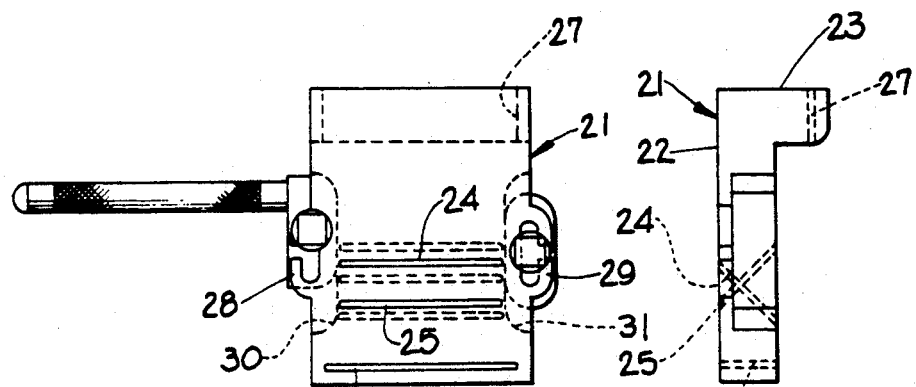
FIG. 6 is an elevational view of the femoral cutting block of the present invention.
FIG. 7 is a side view of the femoral cutting block as seen from the right of FIG. 6.

The femoral cutting block is generally indicated at 21 in FIGS. 6 and 7. The femoral cutting block 21 comprises an L-shaped member having a long leg 22 and a short leg 23. The long leg 22 is provided with a superior slot 24 for making the posterior chamfer cut and an inferior slot 25 for making the anterior chamfer cut. Below slot 25 there is a slot 26 for making the posterior surface cut. Finally, the short leg 23 is provided with a distal femoral articular surface cutting slot 27.

Substantially centrally of the sides of the long leg 22, the femoral cutting block has a pair of slotted lug assemblies 28 and 29. As will be apparent hereinafter, these slotted lug assemblies permit the attachment of the femoral IM rod and the femoral outrigger to the cutting block 21. Immediately behind the lug assemblies 28 and 29, the rear surface of the cutting block 21 is Provided with recesses 30 and 31, respectively, which further serve to accommodate the femoral IM rod and the outrigger, as will be explained hereinafter. The femoral cutting block can be used with either femoral condyle of either leg of the patient. It is provided in three sizes: small, standard and large, and is made of stainless steel.

Figure 8:
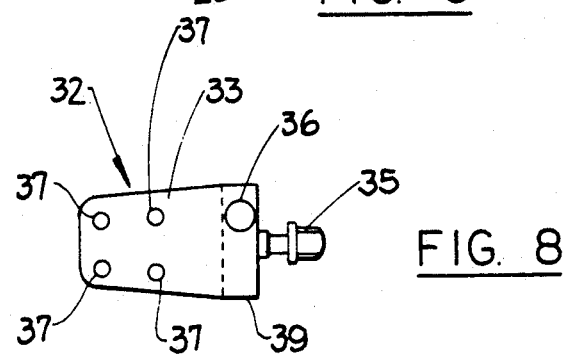
FIG. 8 is an elevational view of the femoral outrigger of the present invention.
Figure 9:
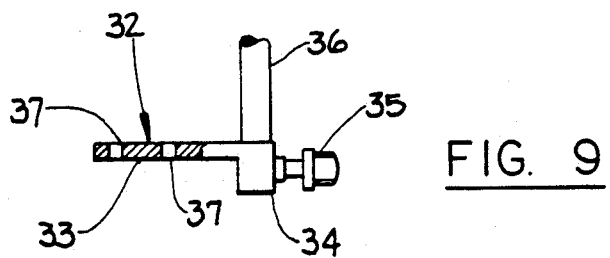
FIG. 9 is an edge view of the femoral outrigger as seen from the bottom of FIG. 8.

FIGS. 8 and 9 illustrate the femoral outrigger of the present invention. The femoral outrigger is generally indicated at 32 and comprises an L-shaped, plate-like member having a long leg 33 and a short leg 34. The short leg 34 is thicker than the long leg 33 and is provided with a central threaded bore 34a (see FIG. 10) adapted to receive a bolt 35 similar to the bolt 13 of the femoral IM rod (see FIG. 3). The bolt 35 is provided with a head adapted to be engaged by a socket wrench.

The short leg 34 is provided with a second threaded bore (not shown). A handle or alignment bar 36 is threadedly engaged in the last mentioned bore and extends perpendicularly to the outside face of long leg 32. Finally, the long leg 32 is provided with four perforations 37, the purpose of which will be apparent hereinafter. The femoral outrigger and its appurtenances are made of stainless steel.

FIG. 10 is an exploded view illustrating the entire femoral cutting guide assembly. It will be apparent from FIG. 10 that the femoral IM rod 7 can be affixed to either side of femoral cutting block 21. In this instance, the shank of bolt 13 is received in the slotted lug assembly 28 and the head 11 of the femoral IM rod will be received in the recess 30 (see FIG. 6) of the femoral cutting block 21. It will similarly be apparent that the outrigger 32 could be attached to either side of the femoral cutting block 21. In this instance, the short leg 34 of outrigger 32 is received within the cutting block recess 31 and the bolt 35, threadedly engaged in the outrigger perforation 34a is received in the slotted lug assembly 29. The slotted lug assemblies 28 and 29 permit adjustment between the femoral IM rod 7, the femoral outrigger 32, and the femoral cutting block 21. Finally, it is evident that the upper leg 20 of the femoral cutting guide locator can be received in the slot 26 of the femoral cutting block 21.

Figure 11:
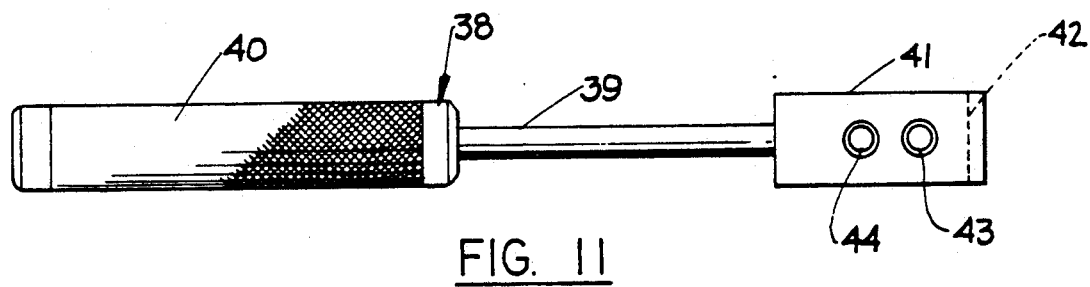
FIG. 11 is an elevational view of the femoral drill guide of the present invention.
Figure 21:
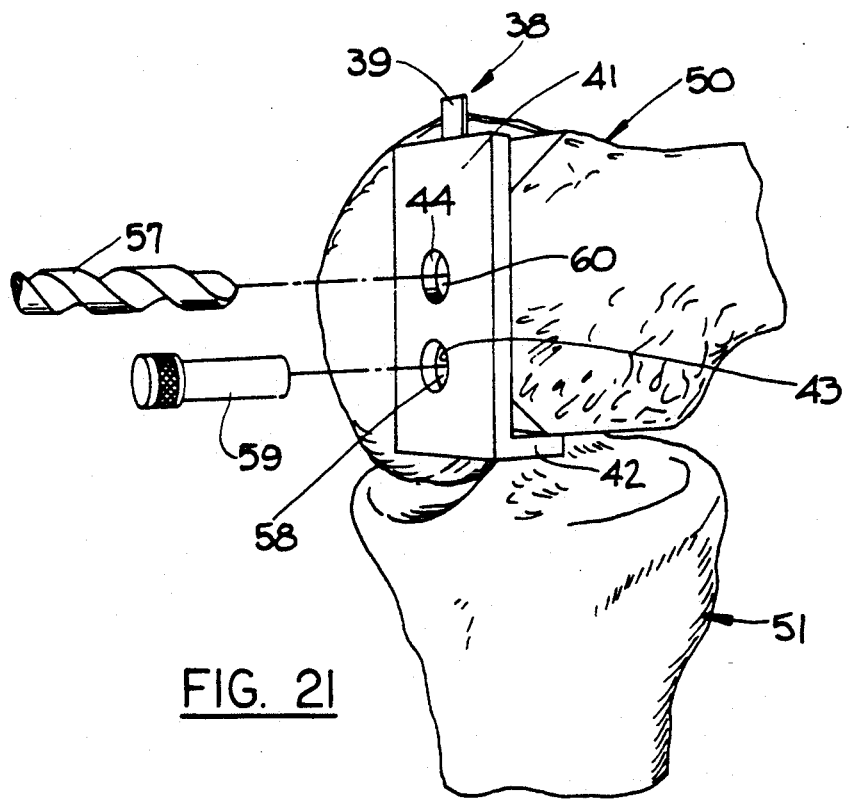
FIG. 21 is a fragmentary perspective view illustrating the use of the femoral drill guide.
Figure 22:
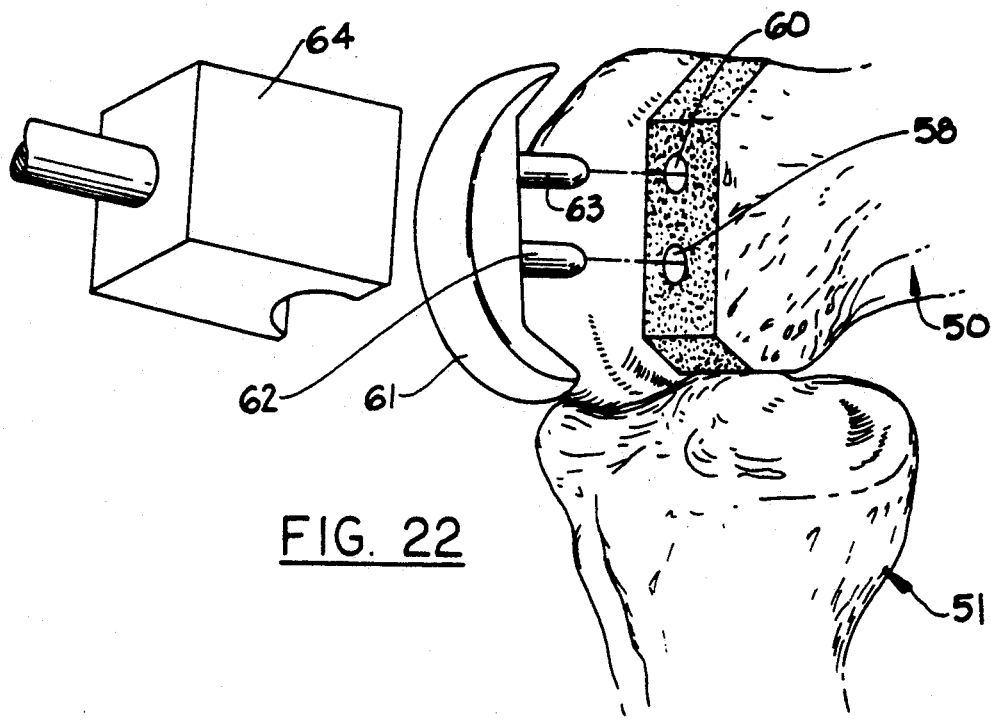
FIG. 22 is a fragmentary perspective view illustrating the placement of a trial femoral component.

FIG. 11 illustrates the femoral drill guide of the present invention. This instrument is generally indicated at 38, is made of stainless steel, and comprises an elongated shank 39 terminating at one end in a knurled handle 40. The other end of shank 39 supports a drill guide template 41. The template 41 comprises a plate-like member terminating at its free end in a rearwardly extending flange 42 (see also FIG. 21). The template 41 has an inferior drill guide bore 43 and a superior drill guide bore 44, the purposes of which will be apparent hereinafter. The femoral drill guide is provided in small, standard and large sizes.

Figure 12:
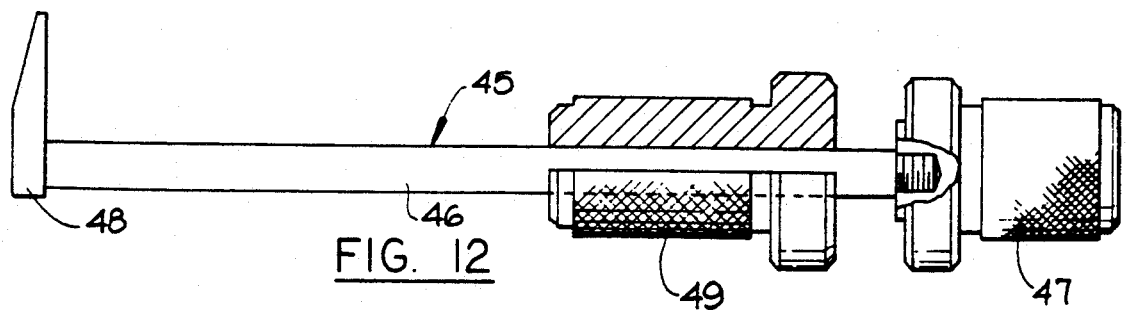
FIG. 12 is an elevational view of the femoral intramedullary rod removal instrument of the present invention.

The final specialized instrument for use in the preparation of the femoral condyle is an IM rod removal tool, generally indicated at 45 in FIG. 12. The IM rod removal tool 45, made of stainless steel, comprises an elongated rod-like shank 46 terminating at one end in a handle element 47 which is threadedly engaged thereon. The other end of shank 45 is provided with a bifurcated claw element 48. Slidably mounted on the shank 46, between the handle element 47 and the claw element 48 there is an impact element 49. The surgeon can cause the impact member 49 to hammer against the handle element 47 so that the IM rod removal tool 45 serves as an extracting tool.

The primary instruments involved having been described, the method for preparing the distal femur to receive the distal femoral prosthesis will now be set forth. For purposes of an exemplary showing, the total replacement of the medial condyle of a patient's right leg will be described. A medial femoral condyle is chosen simply because a medial condyle is more likely to become diseased than a lateral condyle, since the medial condyle bears more of the patient's weight. It will be understood that the steps involved in the treatment of the medial condyle of a patient's right leg would be substantially identical to those involved in the treatment of the lateral condyle of a patient's left leg. Replacement of the lateral condyle of the right leg or the medial condyle of the left leg would differ only in the of left hand instruments rather than right hand instruments in those instances where instruments are provided in both left hand and right hand forms, and in instrument placement, as will be apparent hereinafter.

Figure 13:
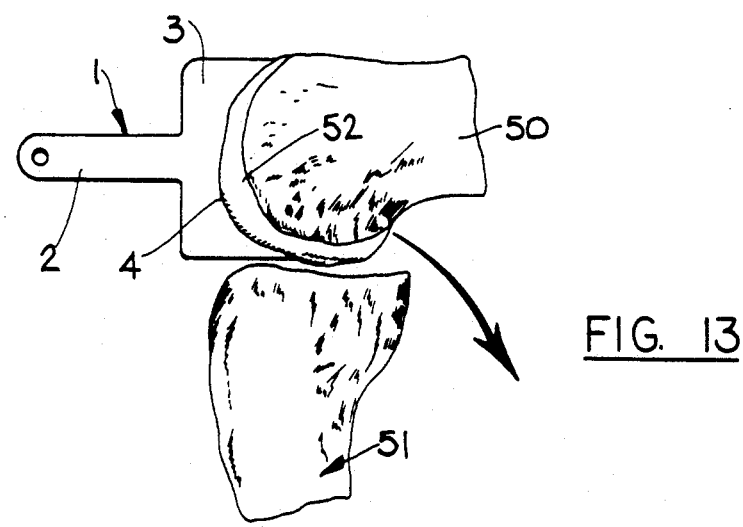
FIG. 13 is a fragmentary elevational view illustrating the use of the femoral template
Figure 14:
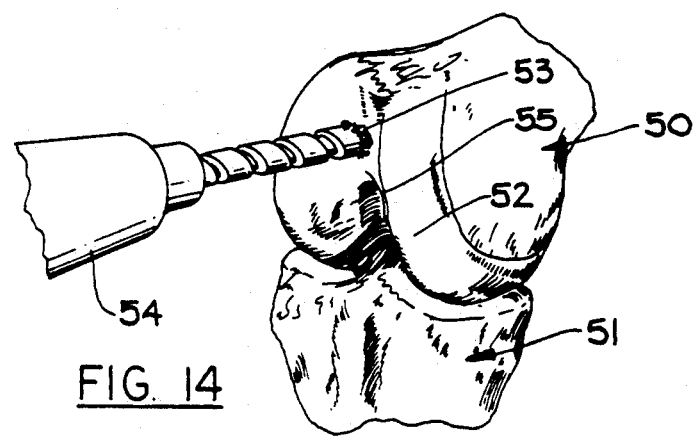
FIG. 14 is a fragmentary perspective view illustrating the drilling of the femur for the intramedullary rod.

The first step in the procedure, of course, is the surgical exposure of the distal end of the femur and the proximal end of the tibia. The surgical procedures for this are well known in the art and do not constitute a part of the present invention. In FIG. 13, the distal end of the femur is generally indicated at 50 and the proximal end of the tibia is generally indicated at 51. The medial condyle to be treated is shown at 52. As a first step, an appropriately sized femoral template 1 has its measuring edge or surface 4 located against condyle 52 to determine the appropriate size (small, standard or large) of the femoral cutting block to be used.

Figure 15:
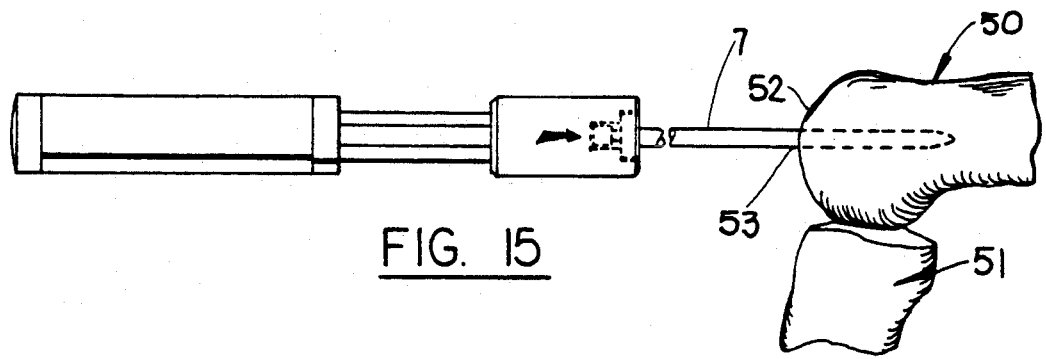
FIG. 15 is a fragmentary elevational view illustrating placement of the intramedullary rod in the femur.

Once this has been determined, an appropriately sized hole 53 is made, utilizing a surgical drill 54, immediately above the intercondylar notch 55. It will be assumed, for purposes of this description, that a standard sized femoral template was selected, as well as a 5° femoral IM rod. The tapered end of the rod is introduced into the drilled hole 53. The femoral IM rod 7 is driven down the femoral shaft. This is shown in FIG. 15.

Figure 16:
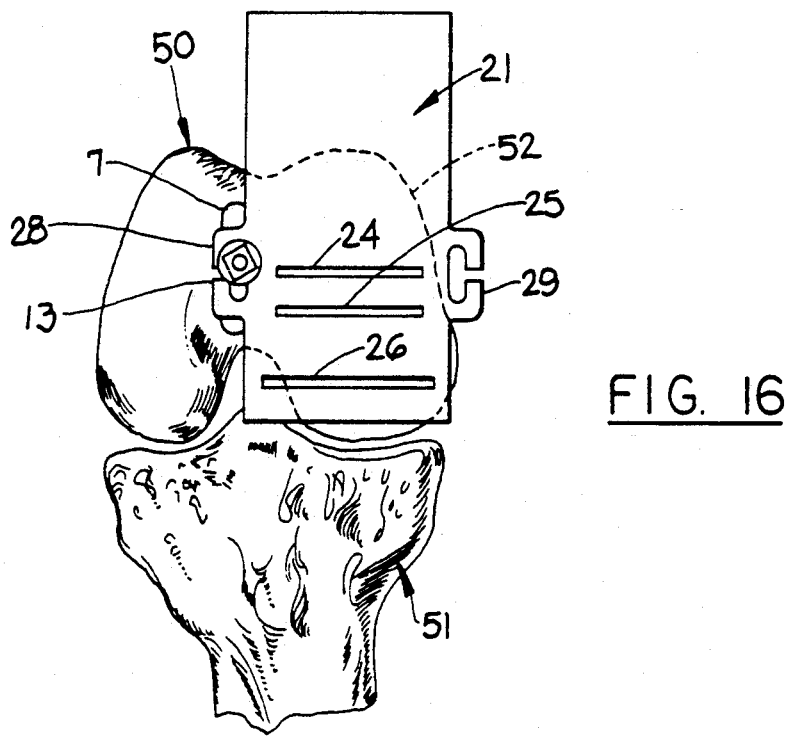
FIG. 16 is a fragmentary elevational view of the femoral cutting block bolted in place

With the femoral IM rod 7 in place, a standard femoral cutting block 21 is mounted thereon, by engaging the femoral IM rod bolt 13 in the slotted lug assembly 28 of the cutting block. At this stage, the bolt 13 is not fully tightened, and the slotted lug assembly 28 will permit shifting of the femoral cutting block 21 to achieve its proper placement. FIG. 16 illustrates the femoral cutting block 21 attached to the femoral IM rod 7.

Figure 17:
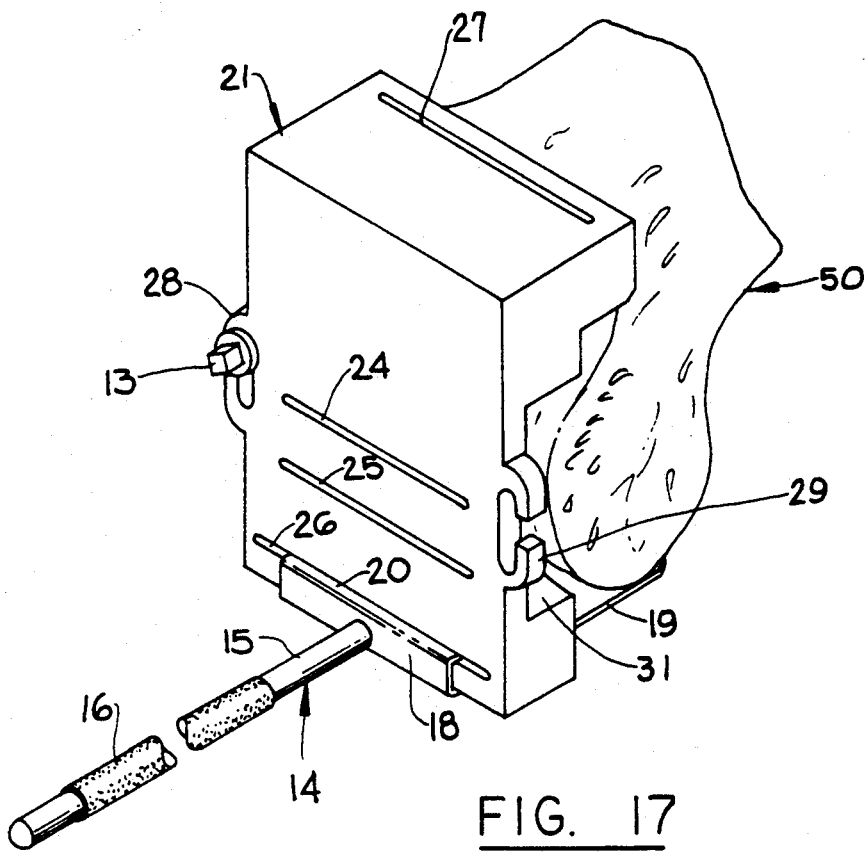
FIG. 17 is a fragmentary perspective view illustrating the use of the femoral cutting guide locator.

Next, the femoral cutting guide locator 14 has its short leg 20 inserted in the posterior surface cutting slot 26. The long leg 19 of the femoral cutting guide locator 14 contacts the posterior condyle to make certain that the position of the femoral cutting block 21 is appropriate in the anterior posterior plane. This is illustrated in FIG. 17.

Figure 18:
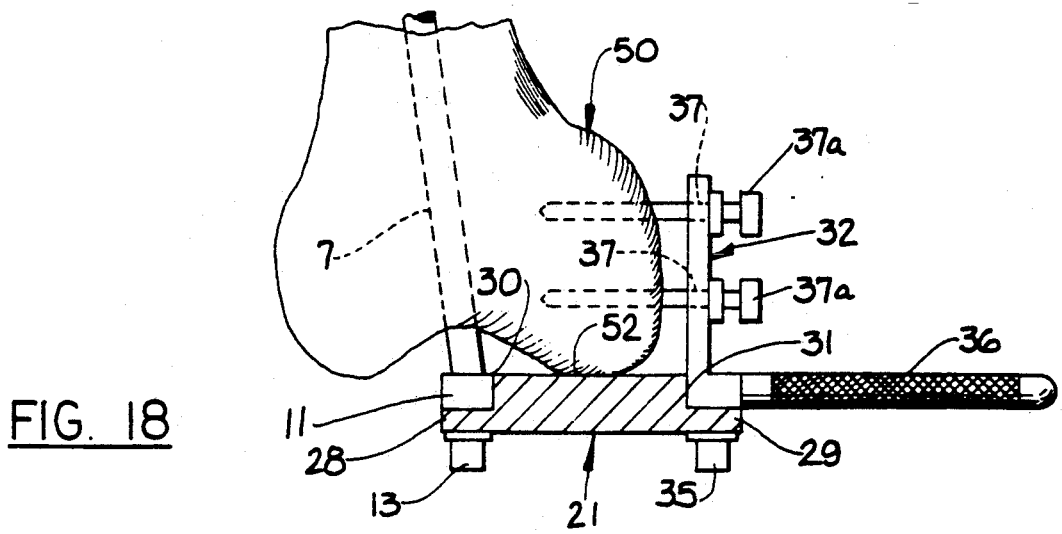
FIG. 18 is a fragmentary top view partly in cross-section, of the femoral cutting block assembly affixed to the femur
Figure 20:
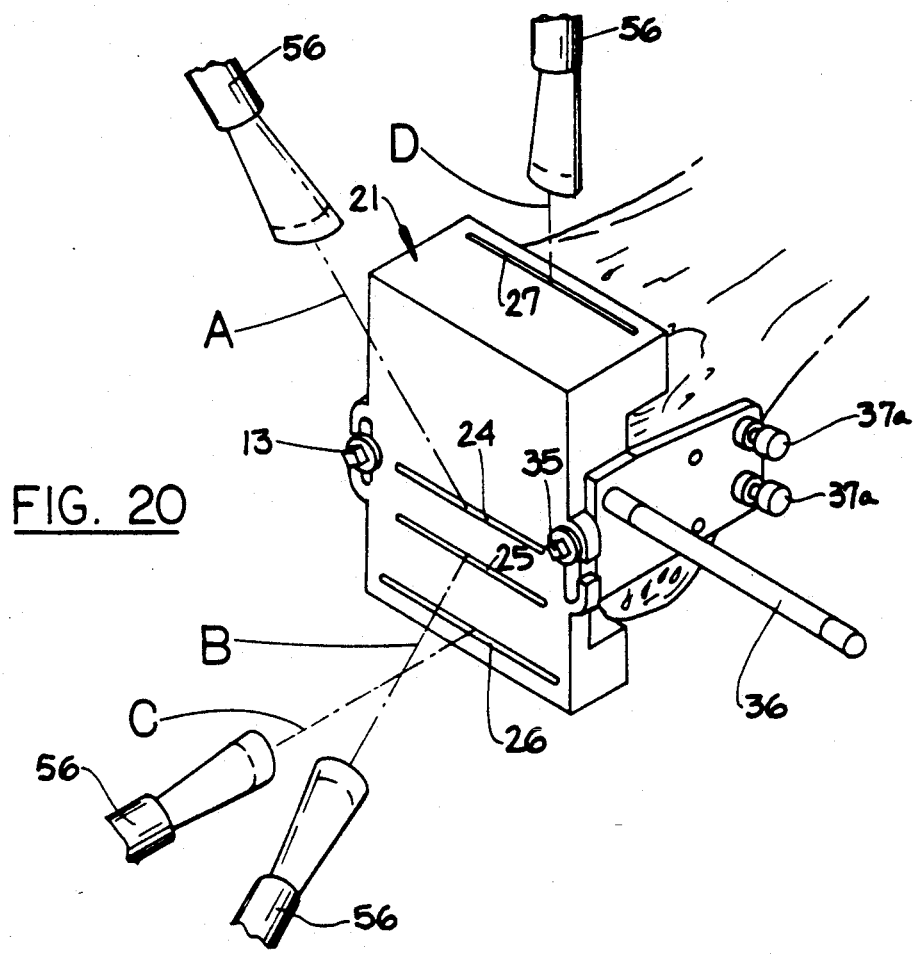
FIG. 20 is a fragmentary perspective view illustrating the femoral cutting block assembly in place for the femoral cuts.

As is shown in FIGS. 18 and 20, the femoral outrigger 32 is thereafter affixed to the femoral cutting block 21 by engaging the outrigger bolt 35 in the slotted lug assembly 29 of cutting block 21. The bolt 35 is fully tightened with the use of a socket wrench. Thereafter, rotational alignment of the axial plane is checked, using the rotational alignment bar or handle 36 on outrigger 32. When properly positioned, this handle or alignment bar 36 should be perpendicular to the shaft of the tibia.

When the femoral cutting block 21 is properly positioned and is flush with the distal femoral condylar surface, the outrigger 32 is fixed to the femur utilizing up to 4 smooth pins 37a impacted firmly into the femoral bone through any of the holes 37 of outrigger 32. The femoral IM rod bolt 13 is then firmly tightened. As a result of the above-noted steps, the femoral cutting block 21 demonstrates excellent stability since it is affixed to the femur itself.

Figure 19:
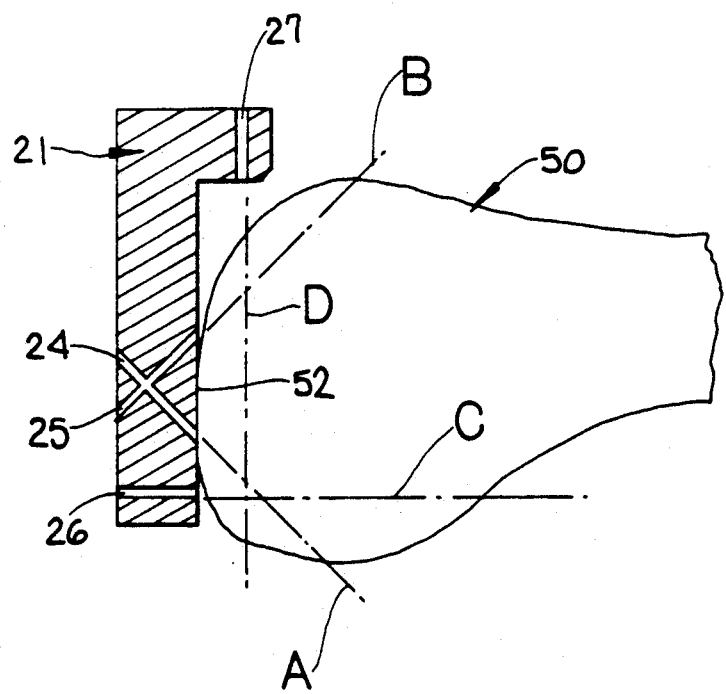
FIG. 19 is a fragmentary semi-diagrammatic view showing the four femoral cuts.

At this point, the surgeon is ready to make the four bony cuts, as indicated in FIG. 20 by the surgical saw 56. In FIGS. 19 and 20, the broken line A represents the superior posterior chamfer cut. The broken line B indicates the inferior anterior chamfer cut. The broken line C indicates the postarticular surface cut and the broken line D designates the distal femoral articular surface cut. These cuts can be made in any order.

Once the four cuts have been made, the outrigger 32 is removed by pulling pins 37a and loosening bolt 35. The cutting block 21 is thereafter removed from the femoral IM rod 7 by loosening bolt 13. Thereafter, the femoral IM rod, itself, is removed by engaging the bifurcated claw element 48 of impacter-disimpacter instrument 45 beneath its head 11 and causing the impact element 49 of the instrument 45 to apply blows to its handle element 47.

With the outrigger 32, femoral cutting block 21 and femoral IM rod 7 removed, the template element 41 of the femoral drill guide 38 is laid along the new surface produced by the distal femoral articular surface cut D. The rearwardly extending flange 42 of template 41 engages the new surface produced by the postarticular cut C. An appropriately sized drill bit 57 is introduced into the drill guide inferior bore 43 and a hole 58 is drilled in the surface created by cut D. A smooth pin 59 is inserted in the drill guide inferior bore 43 and is pounded firmly into bore 58. The drill bit 57 is then introduced into the drill guide superior bore 44 and a second hole 60 is drilled in the surface formed by cut D.

With the holes 58 and 60 drilled, the pin 59 is removed, as is the femoral drill guide 38. At this stage, preparation of the femoral condyle is complete. A metal trial component 61, provided with mounting pegs 62 and 63 may be applied to the prepared condyle to assure a close approximation of the opposed component and condyle surfaces. To this end, mounting peg 62 is inserted in hole 58 and mounting peg 63 is inserted in hole 60, the trial component is then driven to a fully seated position by an appropriate tool 64.

The instrumentation used for preparing the proximal tibia to receive the proximal tibial prosthesis is illustrated in FIGS. 23-30.

Figure 23:
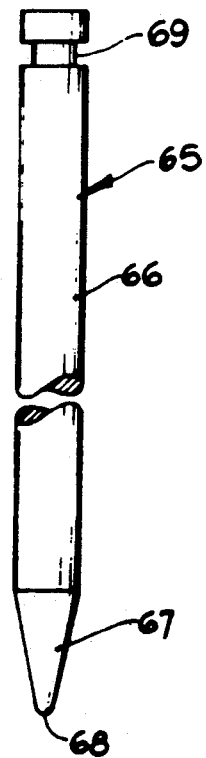
FIG. 23 is a fragmentary elevational view of the tibial intramedullary rod of the present invention.

Turning first to FIG. 23, the tibial intramedullary rod (hereinafter referred to as the tibial IM rod) is generally indicated at 65. The rod has an elongated shank 66 of circular cross-section. The lower end of the shank 66 is tapered as at 67, terminating in a rounded point 68. Just below its upper end, the tibial IM rod is provided with an annular notch 69 so sized as to receive the bifurcated claw element of a tibial IM rod removal tool similar to the tool 45 of FIG. 12. The tibial IM rod 65 is made of stainless steel.

Figure 24:
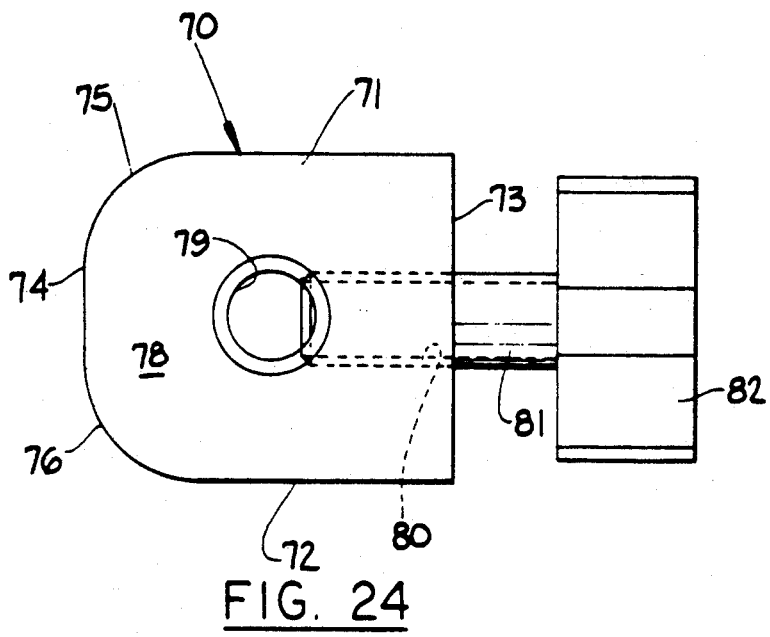
FIG. 24 is a plan view of the vertical tibial cutting block of the present invention.
Figure 25:
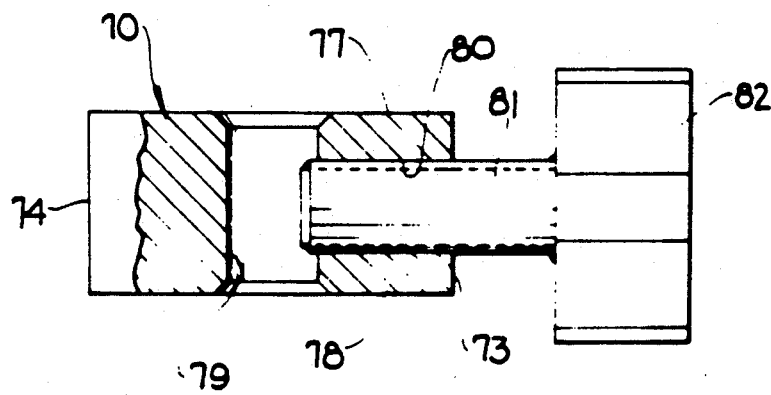
FIG. 25 is a side elevational view, partly in cross-section, of the vertical tibial cutting block of FIG. 24.

FIGS. 24 and 25 illustrate the vertical tibial cutting block, generally indicated at 70. The tibial cutting block 70 has vertical planar sides 71 and 72 together with vertical planar forward and rearward surfaces 73 and 74. The rearward corners are rounded as at 75 and 76.

The tibial cutting block 70 has planar parallel top and bottom surfaces 77 and 78. Centrally of the tibial cutting block 70 there is a vertical bore 79 so sized that it receives the tibial IM rod 65 with a sliding fit. A horizontal threaded bore 80 extends inwardly from the forward surface 73 and intersects the bore 79. The bore 80 receives a set screw 81 provided with a knob 82. The forward face of the knob 82 is provided with a socket 83 (see FIG. 33) for receipt of an Allen wrench.

The vertical tibial cutting block 70 and its set screw 81 are made of stainless steel. The vertical tibial cutting block is made in five predetermined sizes wherein the distance between the vertical sides 71 and 72 and the bore 79 is 4 mm, 6 mm, 8 mm, 10 mm and 12 mm, respectively.

FIGS. 26 and 27 illustrate the stainless steel instrument comprising the tibial marking/drilling template assembly. The tibial marking/drilling template assembly is generally indicated at 84. The instrument comprises an elongated handle 85 having a central knurled portion 86. At one end, the handle 85 supports a right marking/drilling template 87. At the other end, the handle supports a left marking/drilling template 88.

The right template 87 comprises a planar member. The left side 89 of the right template 87 is rectilinear. The right side 90 of the right template approximates the shape of the medial edge of the right side of the tibial prosthesis. The template 87 is provided with a pair of pins 91 and 92 which are essentially flush with or slightly countersunk with respect to the upper surface of the template. The Pins 91 and 92 have pointed lower ends which extend slightly below the bottom surface of the template 87.

The right template 87 has a pair of substantially identical medial and anterior drill guide bores 93 and 94, the purpose of which will be apparent hereinafter. Finally, the right template is provided with a sloping bore 95 which receives a tubular drill bit guide 96. The drill bit guide 96 is flush with the bottom surface of the template and extends upwardly from the upper surface of the template.

The left template 88 is essentially a mirror image of the right template 87, having a rectilinear edge 97 equivalent to the rectilinear edge 89 and an arcuate edge 98 equivalent to the arcuate edge 90. The left template 88 has a pair of medial and anterior drill bit guide bores 99 and 100 equivalent to drill bit guide bores 93 and 94 respectively. Similarly, the left template 88 is provided with pins 101 and 102 identical to pins 91 and 92. Finally, left template 88 is provided with a sloping bore 103 equivalent to bore 95 and provided with a tubular drill bit guide 104 equivalent to the drill bit guide 96.

When the medial condyle of the right leg or the lateral condyle of the left leg is diseased, the right template 87 of instrument 84 will be used. When the medial condyle of the left leg or the lateral condyle of the right leg is diseased, the left template 88 of instrument 84 will be used. The instrument 84 is provided in three sizes: a first having small right and left templates 87 and 88, a second having standard right and left templates 87 and 88, and a third having large right and left templates 87 and 88.

Figure 28:
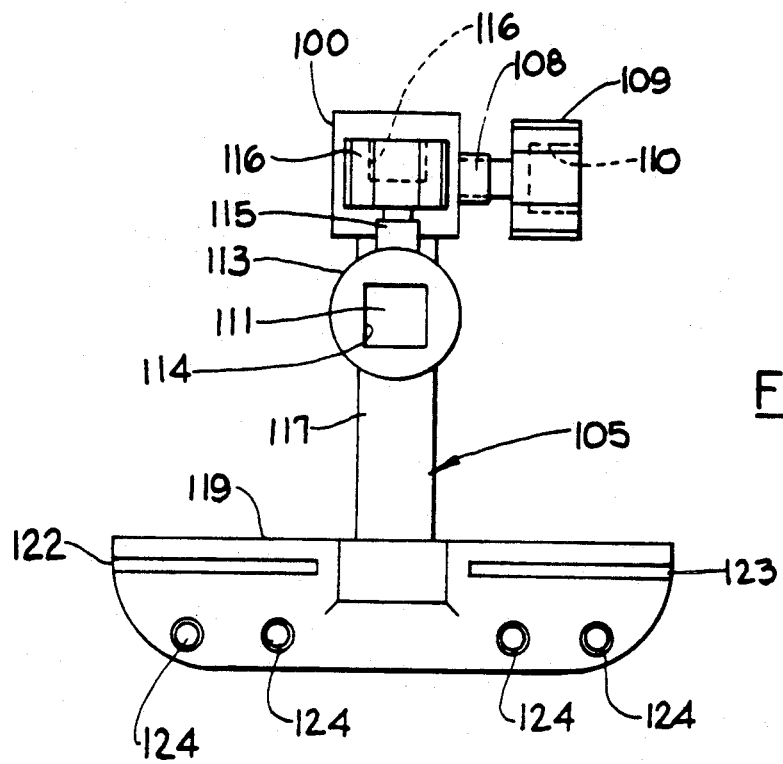
FIG. 28 is an elevational view of the horizontal tibial cutting guide of the present invention.
Figure 29:
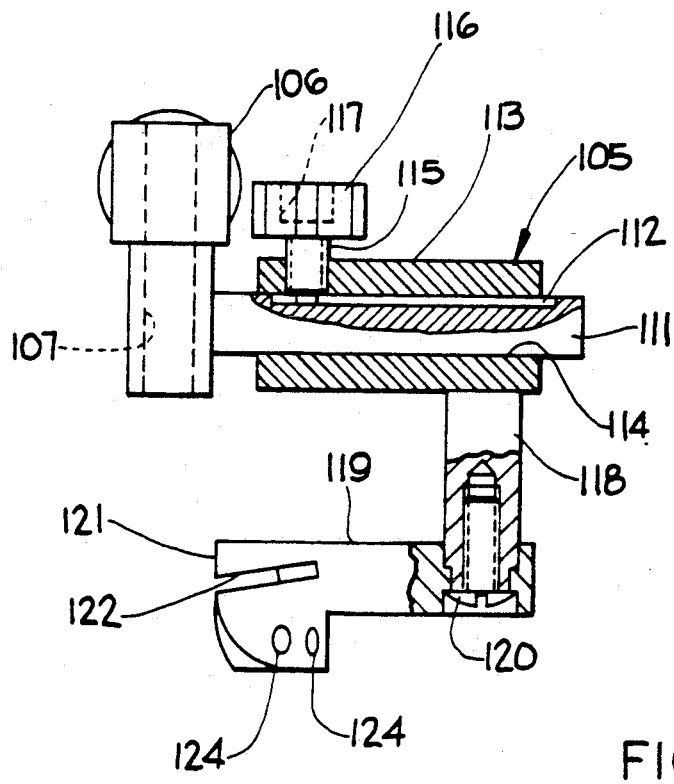
FIG. 29 is a side view of the horizontal tibial cutting guide, partly in cross-section, as seen from the left of FIG. 28.

The stainless steel horizontal tibial cutting guide is illustrated in FIGS. 28 and 29 and is generally indicated at 105. The horizontal tibial cutting guide 105 comprises a vertically oriented sleeve 106 having a bore 107 adapted to receive the tibial IM rod with a sliding fit. The sleeve 106 is provided with a set screw 108, terminating in a knob 109. The knob 109 can be operated manually, and is additionally provided in its front face with a socket 110 for receipt of an Allen wrench. By means of set screw 108, the horizontal tibial cutting guide 105 can be locked in any desired vertical and radial position with respect to the tibial IM rod.

The sleeve 106 supports a laterally extending bar 111 of square cross-section. The upper surface of bar 111 is provided with a longitudinally extending notch 112. Mounted on bar 111 there is a collar 113 provided with a square longitudinal bore 114. The collar is longitudinally shiftable on bar 111. Collar 113 is provided with a set screw 115 terminating in a knob 116 similar to knob 109. The knob 116 is provided in its front face with a socket 117 for receipt of an Allen wrench.

The collar 113 has an integral downwardly depending portion 118 to which the cutting platform 119 is adjustably affixed by a button head cap screw 120 to allow a swiveling action.

The cutting platform 119 has an arcuate surface 121 adapted to face and abut the anterior tibial surface on the operative side. The cutting platform 119 has a pair of cutting guide slots 122 and 123 so that the horizontal tibial cutting guide can be used with respect to either tibial compartment of either leg. The horizontal tibial cutting guide is completed by providing the cutting platform with four holes 124. These holes are adapted to receive smooth pins by which the cutting platform can be temporarily firmly affixed to the tibia, as will be described hereinafter.

FIGS. 30 and 31 illustrate the stainless steel caliper measuring device of the present invention, generally indicated at 125. The caliper measuring device comprises a vertically oriented caliper rod 126. The caliper rod 126 has a longitudinally extending planar surface 127 containing measurement indicia. The caliper rod 126 is slidably mounted in a caliper sleeve 128. Button-like elements 129 and 130 are affixed to the ends of the caliper rod rendering it captive within caliper sleeve 128.

The caliper sleeve 128 is affixed to one end of a support rod 131. The support rod 131, in turn, is slidably received in a horizontal transverse bore 132 in caliper block 133. Thus, the caliper sleeve 128 and caliper rod 126 can be shifted toward and away from caliper block 133.

Caliper block 133 has a vertical bore 134 adapted to slidably receive the tibial IM rod 65. It will be noted from FIG. 31 that the horizontal transverse bore 132 for the caliper sleeve support rod 131 intersects the vertical bore 134. The bore 134 is also intersected by a horizontal threaded bore 135 mounting a set screw 136 provided with a knob 137. The knob 137 can be manipulated by hand and is also provided with a forwardly facing socket 138 for the receipt of an Allen wrench.

From the above description, it will be apparent that the caliper rod 126 can not only be shifted toward and away from caliper block 133, but also can be rotated about the tibial IM rod 65. Furthermore, the caliper sleeve support rod 131 can be shifted vertically along the tibial IM rod 65. When the caliper rod 126 is positioned as desired, and the upper edge of the caliper sleeve is located adjacent the desired measurement indicia on flat 127, the knob 137 can be tightened. It will be evident from FIG. 31 that the knob 137 will lock both the tibial IM rod 65 and the caliper sleeve support rod 131 within the caliper block 133.

The vertical tibial cutting block 70, the horizontal tibial cutting guide 105, the caliper measuring device 125 and the tibial IM rod 65 constitute a tibial cutting guide assembly, as will be apparent.

The primary instruments used in the preparation of the tibial compartment having been described, the steps involved in the tibial compartment preparation can now be set forth. Again, like parts have been given like index numerals.

Figure 32:
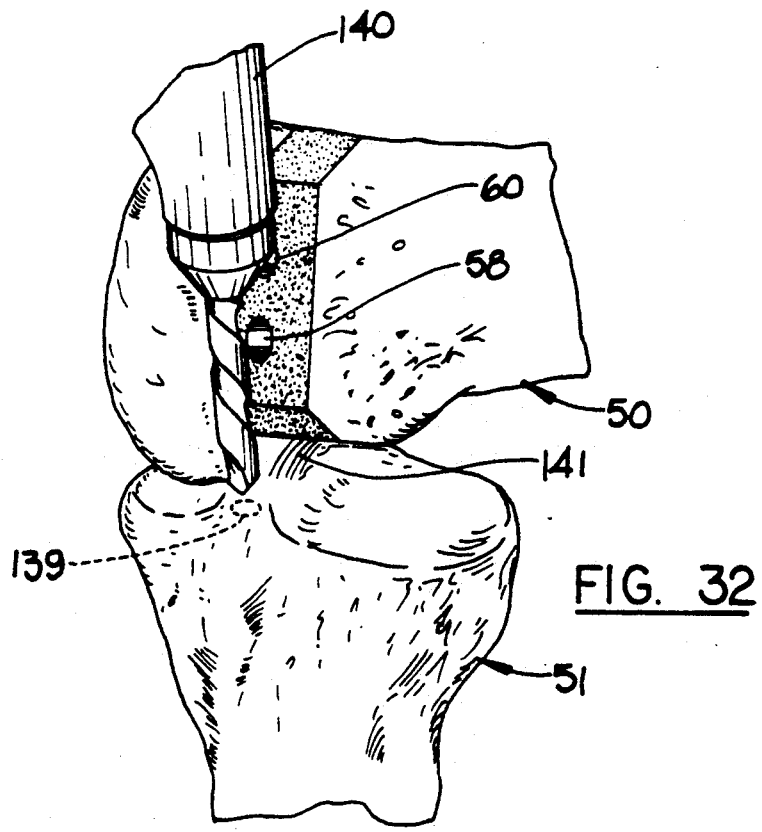
FIG. 32 is a fragmentary perspective view illustrating the drilling of the tibia for the tibial intramedullary rod.

FIG. 32 illustrates the first step in the preparation of the tibial compartment. A hole (indicated in broken lines at 139) is drilled by surgical drill 140 for placement of the tibial IM rod 65. The hole 139 is so located as to avoid the anterior cruciate ligament insertion in the tibial plateau. The cruciate ligament is shown at 141 in FIG. 32.

The tibial IM rod is then impacted through hole 139 and down the tibial shaft, with care being taken to avoid varus or valgus angulation of the tibial IM rod during impaction. FIG 33 illustrates the tibular IM rod 65 in place. It will be noted that more than 50% of the tibular IM rod has been driven into the tibial shaft.

A natural 5° posterior inclination of the tibial IM rod will result due to the anterior placement of the tibial IM rod to avoid injuring the anterior cruciate ligament. This 5° posterior tilt of the tibial IM rod will be accommodated by the horizontal tibial cutting guide 105 of FIGS. 28 and 29. It will be noted in FIG. 29 that the cutting guide slots 22 and 23 slope slightly to make up for the posterior tilt of the tibial IM rod.

Reference is now made to FIG. 34. With the tibial IM rod 65 in place, the appropriate template (in this instance the right template 87) of an appropriately sized tibial marking/drilling template assembly 84 is placed on the tibial plateau with its arcuate edge 90 placed flush with the medial edge of the tibial cortex. The distance E between the tibial IM rod and the rectilinear edge 89 of the tibial marking/drilling template assembly is marked, directly on the tibia utilizing a cutting cautery. Such a mark is shown in FIG. 34 at 141. Once the mark 141 has been made, the tibial marking/drilling template assembly is removed. The distance E is used to select the appropriately sized tibial cutting block (see FIGS. 24 and 25). If the distance E, for example, is approximately 8 mm, then an 8 mm tibial cutting block is selected. As is shown in FIG. 35, the appropriately sized vertical tibial cutting block is mounted on the tibial IM rod 65 and located flush with the cortex of the tibia. At this point, the set screw 81 of the tibial cutting block 70 is tightened by insertion of an Allen wrench (not shown) into the socket 83 of knob 82.

Figure 36:
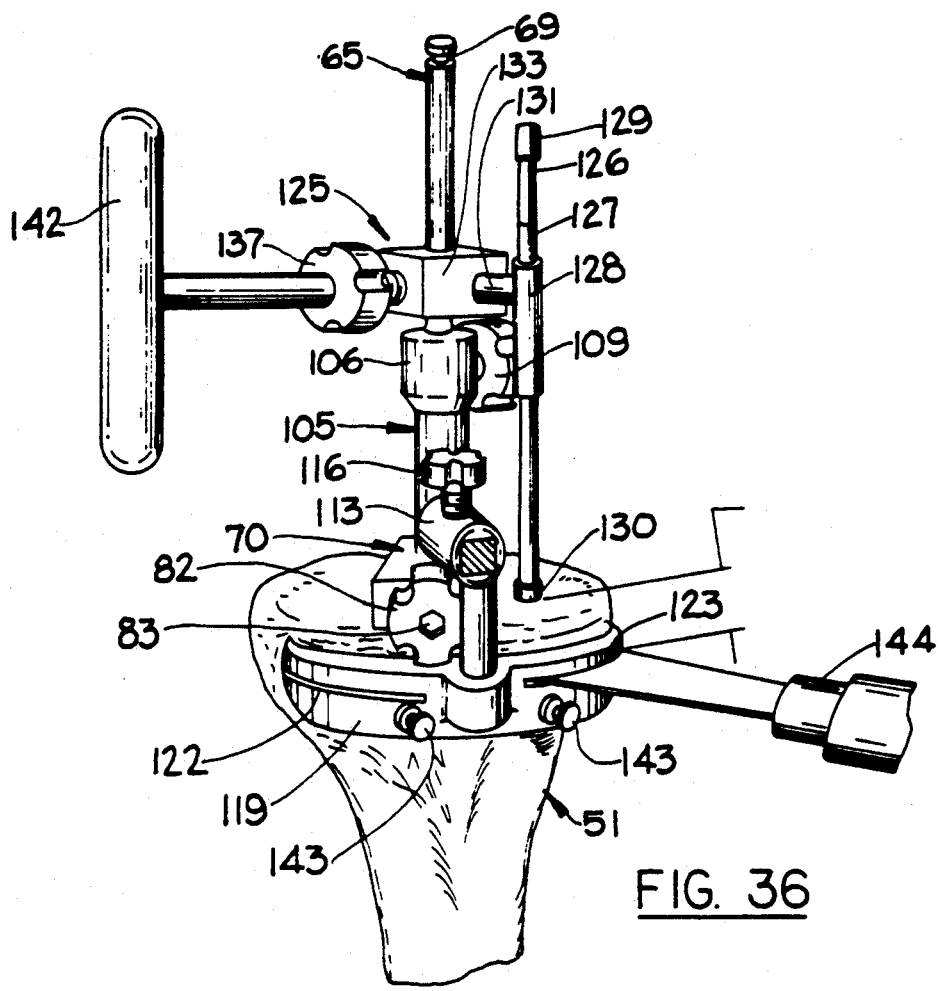
FIG. 36 is a fragmentary perspective view illustrating the horizontal tibial cutting guide and the horizontal tibial cut being made.

The next series of steps are illustrated in FIG. 36. With the vertical tibial cutting block 70 in place, the horizontal tibial cutting guide is next mounted by placing its sleeve 106 over the tibular IM rod 65. If required, the collar 113 may be adjusted by knob 116 so that the cutting platform 119 can be properly positioned with respect to the tibia. The cutting platform 119 can also be rotated horizontally about the tibial IM rod 65 to achieve its proper position since the sleeve knob 109 has not yet been tightened. Thus, the horizontal tibial cutting guide is fully adjustable, capable of being rotated about the tibial IM rod and shifted both vertically and horizontally to bring the cutting platform 119 in proper position against the anterior tibial surface on the operative side. With the horizontal tibial cutting guide 105 still loose on the tibular IM rod 65, the caliper measuring device 125 is located in place by causing the tibular IM rod 65 to extend upwardly through the perforation 134 in caliper block 133. By appropriate rotation of the caliper block 133 about the tibular IM rod 65 and by appropriate adjustment of the caliper sleeve supporting rod 131 in caliper block bore 132 the caliper rod 126 is so located that its bottom end 130 contacts the central, most depressed, portion of the tibial plateau. The caliper sleeve 128 is raised or lowered (as required) until its upper edge aligns with the 8 mm mark on the caliper rod flat 127. The use of the 8 mm mark is preferred so that the least amount of bone is removed from the medial tibial compartment. If the tibial plateau is so damaged that more bone must be removed, the upper edge of the caliper sleeve 128 is aligned with the 10 mm or the 12 mm mark. The 8 mm, 10 mm and 12 mm marks correspond to the relative location of the cutting platform 119 and correlate with the overall thickness of the tibial tray to be mounted on the plateau and the three sizes of inserts available for use with the tibial tray.

It will be understood that as the vertical position of the caliper sleeve 128 is adjusted to the surgeon's satisfaction, a similar adjustment of the caliper block 133 with respect to the tibial IM rod will simultaneously be made. When adjustments are completed, the caliper block knob 137 is tightened with an Allen wrench 142, locking the caliper block 133 in position on the tibular IM rod 65.

At this stage, the final adjustment of the tibial horizontal cutting guide can be made by simply shifting the horizontal cutting guide sleeve 106 upwardly on the tibial IM rod 65 until its upper end abuts the lower end of caliper block 133. At this point, the knob 109 is tightened with an Allen wrench to lock the tibial horizontal cutting guide in final position. A pair of smooth pins 143 are impacted into the tibia through two of the perforations 124 of the cutting platform 119.

At this point, the instrumentation is ready for the horizontal tibial cut to be made. Since, in the example described, the medial tibial compartment is being prepared, the cut is made by inserting a surgical saw 144 through the guide slot 123 of cutting platform 119.

With the horizontal tibial cut completed, the caliper measuring device 125 is removed from the tibial IM rod 65 by loosening knob 137. Thereafter, the pins 143 extending through the cutting platform 119 are removed. At this point, the knob 109 is loosened, and the horizontal tibial cutting guide 105 is removed from the tibial IM rod 65.

Figure 37:
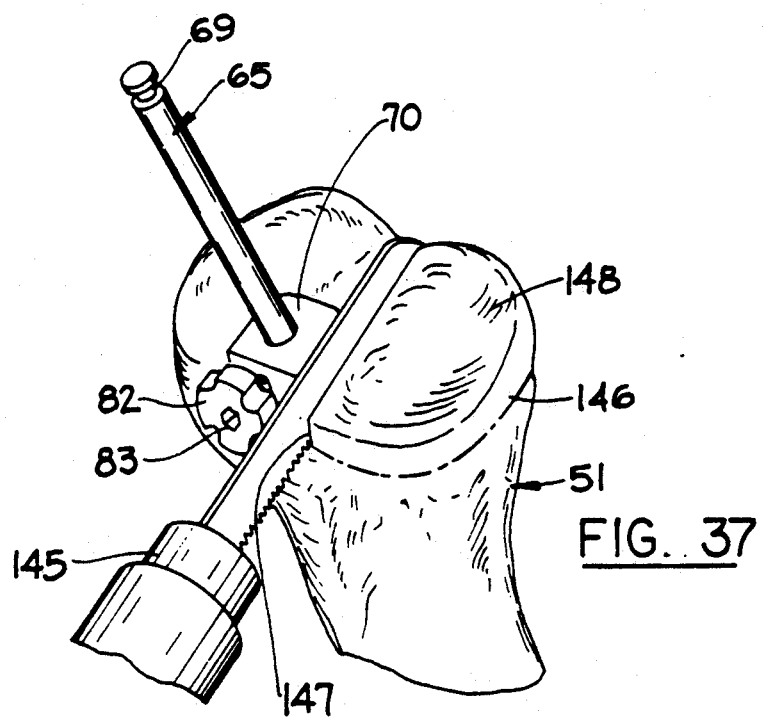
FIG. 37 is a fragmentary perspective view illustrating the use of the vertical tibial cutting block in making the vertical tibial cut.
Figure 38:
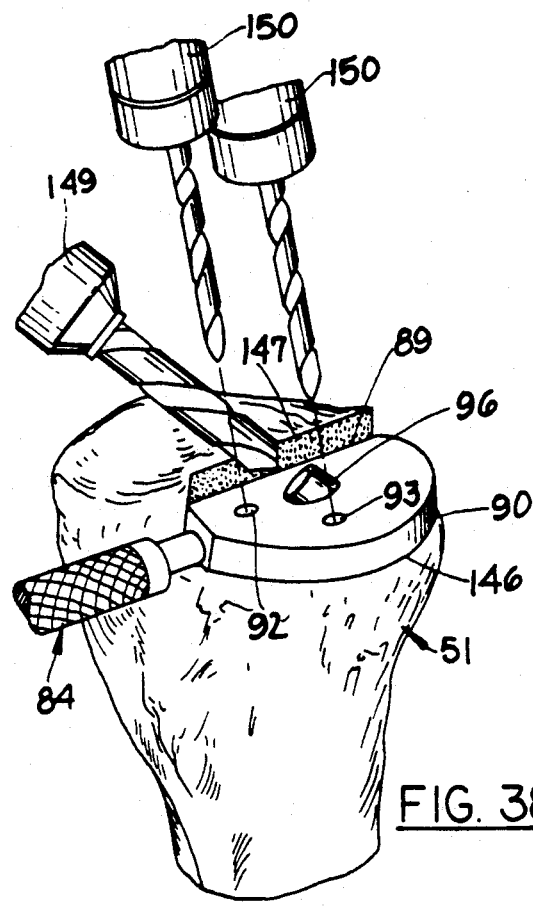
FIG. 38 is a fragmentary perspective view illustrating the use of the tibial marking/drilling template assembly for drilling in preparation for the fixation of the tibial tray.
Figure 39:
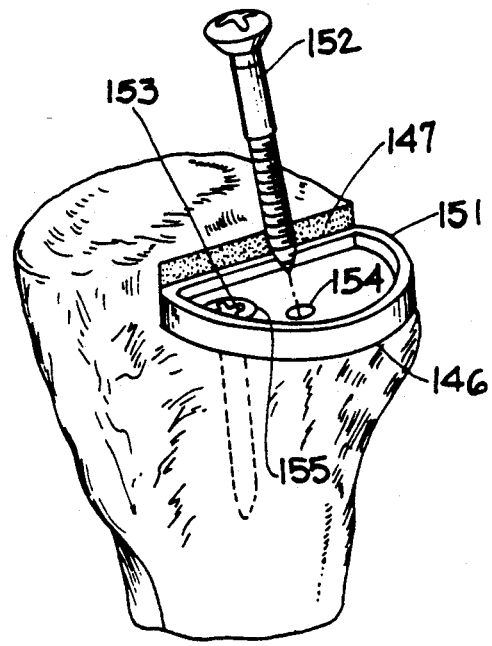
FIG. 39 is a fragmentary perspective view illustrating the fixation of the tibial tray.

With the caliper measuring device 125 and the horizontal tibial cutting guide 105 removed, the surgeon is now free to make the vertical tibial cut, as illustrated in FIG. 37. To this end, an appropriate reciprocating surgical saw 145 is located with its blade flush against the appropriate side surface of vertical tibial cutting block 70. In FIG. 37, the horizontal cut is indicated by broken line 146. The vertical cut is indicated at 147. When both the vertical and horizontal cuts have been completed, the bony segment 148 is removed. The vertical tibial cutting block 70 and the tibial IM rod 65 are removed.

Upon removal of the bony part 147, the tibial marking/drilling template assembly 84 (again of the proper size) has its right template 87 placed over the cut tibial surface with its arcuate side 90 again flush with the medial edge of the tibial cortex and its rectilinear side 89 abutting the vertical cut 147. The template 87 is impacted to assure that its small pins 91 and 92 imbed in the cut bone surface for stability. Thereafter, an oblique drill hole is made by means of a surgical drill 149, utilizing the angled tubular drill bit guide 96. The oblique drill hole is made to receive the tibial tray peg. Another surgical drill 150 is used to drill a hole through the medial template hole 93, aligning the drill to penetrate the cortex medially. The drill 150 is thereafter used to drill a hole through the anterior template drill guide hole 92. This anterior drill hole is made vertically, or angled anteriorly if cortical fixation by the screw is preferred.

At this point, a tibial tray 151 is selected, identical in size to the template 87. The tibial tray 151 is located on the cut tibial surface with the peg (not shown) of the tibial tray located in the oblique hole made by drill 149. The tibial tray 151 is impacted in place. Thereafter, screws 152 and 153 are located in countersunk holes 154 and 155 in the tibial tray and screwed into the medial and anterior drill holes made by surgical drill 150. The heads of screws 152 and 153 will be flush with the upper bottom surface of the tibial tray 151.

Figure 40:
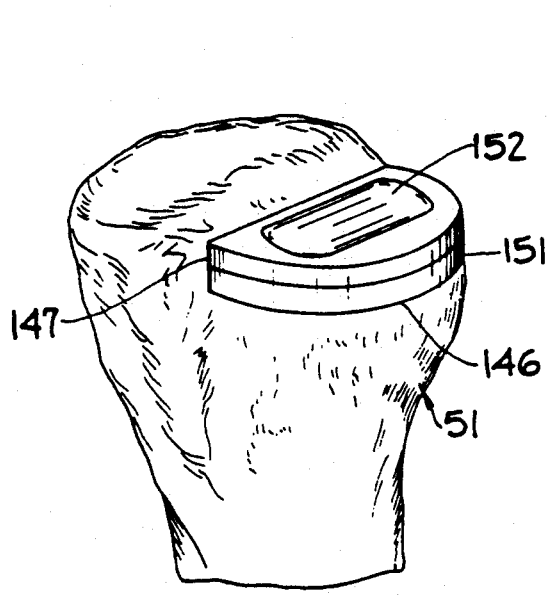
FIG. 40 is a fragmentary perspective view, similar to FIG. 37, illustrating the tibial insert mounted in the tibial tray.
Figure 41:
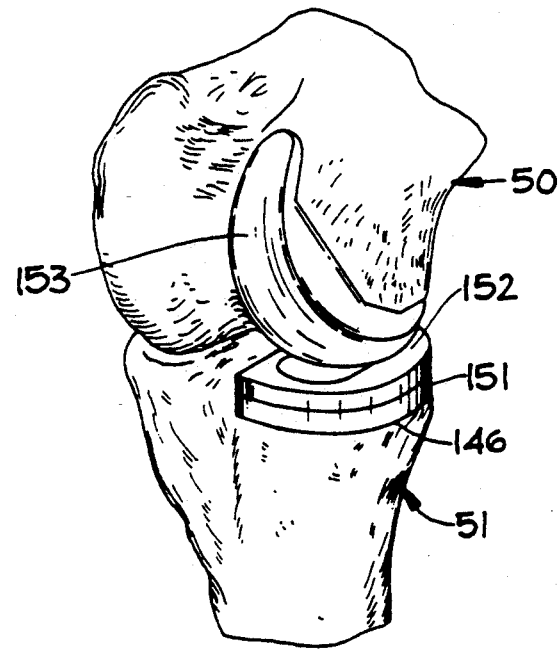
FIG. 41 is a fragmentary perspective view illustrating both the femoral and tibial components in place.

At this point, a black plastic, slightly undersized, tibial trial implant can be placed within the tibial tray 146. The tibial tray and trial implant should correlate with the amount of bone removed, as determined by the caliper measuring device 125 at the time of the tibial resection. The trial femoral component can then also be placed on the femur. In mild flexion there should be approximately a 2 mm to 3 mm gap between the components with valgus stress. Thereafter, the trial components are removed and the appropriate height polyethylene tibial insert 152 is impacted in place in the tibial tray 151, as shown in FIG. 40. The permanent femoral component 153 is then appropriately mounted as shown in FIG. 41. Tracking is noted throughout full flexion and extension. At this stage, the replacement procedure is complete. Closing and postoperative procedures are substantially conventional and do not constitute a part of the present invention.

From the above description it will be apparent that the same instrumentation can be used when the lateral tibial compartment is to be treated The mounting of the tibial IM rod is identical. Selection of an appropriately sized vertical tibial cutting guide is made in the same manner using the left template 88 of the tibial marking/drilling template assembly 84. The use of the horizontal tibial cutting guide 105 and the caliper measuring device 125 is the same, the caliper block 133 being rotated on the tibial IM rod so that the caliper rod cooperates with lateral tibial plateau. The horizontal and vertical tibial cuts are made using the slot 122 of the cutting guide 119 and using the appropriate side of the vertical cutting block 70. The holes are drilled in the horizontal cut surface of the tibia using the left template of instrument 84. Thereafter, an appropriately sized lateral tibial tray and insert are installed.

It is within the scope of the invention to glue the femoral and tibial components in place. When the tibial tray 151 is glued in place, screws 152 and 153 might not be used. The holes 154 and 155 in the tibial tray are provided with plastic plugs to prevent glue from entering that part of the tibial tray in which insert 152 is mounted.

Modifications may be made in the invention without departing from the spirit of it.

What is claimed is:

1. A method of replacing the articulating tibial surface of a knee joint in which the diseased area is restricted to one of the medial and lateral compartments, said method comprising the steps of drilling a hole in the tibia anterior of the anterior cruciate ligament insertion, inserting a tibial IM rod in said hole and down the center of the tibia, providing an appropriately sized vertical tibial cutting block having a pair of vertical parallel sides comprising vertical medial and lateral cutting guide surfaces, said vertical tibial cutting block having a vertical perforation adapted to slidingly receive said free end of said tibial IM rod, adjustably mounting said vertical tibial cutting block on said free end of said tibial IM rod, providing a horizontal tibial cutting guide having a vertical sleeve with a bore to slidingly receive said free end of said tibial IM rod, said sleeve supporting a cutting platform having medial and lateral cutting guide slots therein, mounting said horizontal tibial cutting guide sleeve on said tibial IM rod above said vertical tibial cutting block, providing a caliper measuring device adjustably mountable on the free end of said tibial IM rod and having a vertical caliper rod to contact the affected tibial plateau and marked with indicia corresponding to the position of said tibial horizontal cutting guide, determining the desired vertical position of said horizontal tibial cutting guide, setting said caliper measuring device accordingly and fixing said caliper measuring device on said tibial IM rod, locating said horizontal tibial cutting guide at the desired position by causing its sleeve to abut a portion of said caliper measuring device and fixing said sleeve on said tibial IM rod, affixing said cutting platform to the tibia with smooth pins, performing said horizontal tibial cut using the appropriate one of said medial and lateral cutting guide slots, removing said caliper measuring device and said horizontal tibial cutting guide from said tibial IM rod, performing said tibial vertical cut adjacent said vertical tibial cutting block, removing the cut bony part, removing said vertical tibial cutting block and said tibial IM rod, providing a tibial prosthesis comprising an appropriately sized and shaped tibial tray with a mounting peg and an appropriately sized and shaped tibial bearing insert mountable in said tray, mounting said tibial tray on said horizontal tibial cut surface, mounting said tibial bearing insert in said tibial tray.

2. The method claimed in claim 1 wherein said tibial tray is provided with an obliquely angled mounting peg, and including the steps of providing a tibial template assembly comprising a handle terminating at its ends in right and left mirror image tibial templates, said templates each having upper and lower surfaces, a rectilinear side surface and an arcuate side surface approximating the shape of the tibial cortex, each template has a pair of short pointed pins extending downwardly from its lower surface and an obliquely oriented tubular surgical drill bit guide extending through said template, said tubular guide extending upwardly from said template upper surface and being flush with said template lower surface, locating the appropriate template over the tibial horizontal cut surface and impacting it flush therewith, drilling a hole into the tibial horizontal cut surface using said tubular drill bit guide, removing said template and affixing said tibial tray to said tibial horizontal cut surface with said tibial tray mounting peg located in said drilled tibial hole.

3. The method claimed in claim 2 including the step of applying bone adhesive between said tibial tray and said tibial horizontal cut surface.

4. The method claimed in claim 2 including the steps of providing each of said right and left tibial templates with medial and anterior surgical drill bit guide holes, providing said tibial tray with corresponding medial and anterior perforations, drilling medial and anterior holes in said tibial horizontal cut surface using said medial and anterior drill bit guide holes of said appropriate template, and mounting screws in said tibial tray and horizontal cut surface medial and anterior holes.

5. The method claimed in claim 2 including the step of locating said appropriate tibial template on said tibial plateau after mounting said tibial IM rod with said template arcuate side surface aligned with the medial edge of the tibial cortex, measuring the distance between said rectilinear template side surface and said tibial IM rod, and selecting an appropriately sized vertical tibial cutting block in accordance with said measurement.

6. A method of replacing the articulating femoral and tibial surfaces of a knee joint in which the diseased area is restricted to one of the medial and lateral compartments, said method comprising the steps of measuring the size of the affected condyle, drilling a hole immediately superior to this intercondylar notch, inserting as femoral IM rod in said hole and down the center of the femur, selecting an appropriately sized femoral cutting block having surgical saw blade guide slots for the posterior and distal articular surface cuts and the posterior and anterior chamber cuts, adjustably bolting one side of said femoral cutting block to the free end of said femoral IM rod, adjustably securing an outrigger plate to the other side of said femoral cutting block, securing the free end of said outrigger plate to the femur with smooth pins, performing all of said femoral cuts in any order, removing said outrigger plate, said femoral cutting block and said femoral IM rod selecting a conventional femoral prosthesis, and mounting said femoral prosthesis on said femoral cut surfaces, drilling a hole in the tibia anterior of the anterior cruciate ligament insertion, inserting a tibial IM rod in said hole and down the center of the tibia, providing an appropriately sized vertical tibial cutting block having a pair of vertical parallel sides comprising vertical medial and laterail cutting guide surfaces, said vertical tibial cutting block having a vertical perforation adapted to slidingly receive free end of said tibial IM rod, adjustably mounting said vertical tibial cutting block on said free end of said tibial IM rod, providing a horizontal tibial cutting guide having a vertical sleeve with a bore to slidingly receive said free end of said tibial IM rod, said sleeve supporting a cutting platform having medial and lateral cutting guide slots therein, mounting said horizontal tibial cutting guide sleeve on said tibial IM rod above said vertical tibial cutting block, providing a caliper measuring device adjustably mountable on the free end of said tibial IM rod and having a vertical caliper rod to contact the affect tibial plateau and marked with indicia corresponding to the position of said tibial horizontal cutting guide, determining the desired vertical position of said horizontal tibial cutting guide, setting said caliper measuring device accordingly and fixing said caliper measuring device on said tibial IM rod, locating said horizontal tibial cutting guide at the desired position by causing its sleeve to abut a portion of said caliper measuring device and fixing said sleeve on said tibial IM rod, affixing said cutting platform to the tibia with smooth pins, performing said horizontal tibial cut using the appropriate one of said medial and lateral cutting guide slots, removing said caliper measuring device and said horizontal tibial cutting guide from said tibial IM rod, performing said tibial vertical cut adjacent said vertical tibial cutting block, removing the cut bony part, removing said vertical tibial cutting block and said tibial IM rod, providing a tibial prosthesis comprising an appropriately sized and shaped tibial tray with a mounting peg and an appropriately sized and shaped tibial bearing insert mountable in said tray, mounting said tibial tray on said horizontal tibial cut surface, mounting said tibial bearing insert in said tibial tray.

7. The method claimed in claim 6 including the steps of providing a planar plate-like femoral template having a handle portion and a head portion, said head portion having a substantially arcuate measuring edge terminating in posterior and anterior ends, and placing said femoral template measuring edge against said affected femoral condyle to determine the size of the femoral cutting block to be used.

8. The method claimed in claim 6 including the steps of providing said free end of said femoral IM rod with a head, a threaded bore in said head and a bolt threadedly engaged in said threaded bore for affixing said femoral cutting block to said IM rod, said head and bolt being angularly related to the long axis of said femoral IM rod at one of 3°, 5° and 7°, and selecting a femoral IM rod having the appropriately angled head and bolt for each individual patent.

9. The method claimed in claim 6 including the steps of providing a femoral cutting block locating instrument comprising a handle supporting at one end a plate-like member formed into a U-shape having a base portion to which said handle is affixed and a short leg and a long leg in parallel spaced relationship, inserting said short leg of said instrument into the posterior articular surface cut slot of said femoral cutting block with said long leg extending rearwardly past the adjacent end of said femoral cutting block, causing said long leg of said instrument to contact the femoral posterior condyle to adjust said femoral cutting block in the anterior posterior plane, and thereafter removing said instrument.

10. The method claimed in claim 6 wherein said outrigger plate has a planar surface facing away from said diseased condyle, and including the steps of affixing a rod-like handle/alignment bar to said outrigger plate extending perpendicularly from said face thereof, and using said handle/alignment bar to adjust the rotational alignment of said femoral cutting block.

11. The method claimed in claim 6 wherein said femoral prosthesis is provided with two mounting pegs, and including the steps of providing a femoral drill guide comprising a handle supporting a planar template having a superior and an inferior drill bit guide perforation and an end portion extending perpendicularly from said template, locating said template centrally over said femoral distal articular surface cut with said template end portion overlying said femoral posterior articular surface cut, drilling an inferior hole in said femoral distal articular surface cut using said inferior template drill bit guide perforation, inserting a smooth pin through said inferior template drill bit guide perforation and into said inferior hole, drilling a superior hole in said femoral distal articular surface cut using said superior template drill bit guide perforation, and removing said pin and said femoral drill guide.

12. The method claimed in claim 11 including the step of applying bone adhesive between said femur and said femoral prostheses.

13. The method claimed in claim 6 wherein said tibial tray is provided with an obliquely angled mounting peg, and including the steps of providing a tibial template assembly comprising a handle terminating at its ends in right and left mirror image tibial templates, said templates each having upper and lower surfaces, a rectilinear side surface and an arcuate side surface approximating the shape of the tibial cortex, each template has a pair of short pointed pins extending downwardly from its lower surface and an obliquely oriented tubular surgical drill bit guide extending through said template, said tubular guide extending upwardly from said template upper surface and being flush with said template lower surface, locating the appropriate template over the tibial horizontal cut surface and impacting it flush therewith, drilling a hole into the tibial horizontal cut surface using said tubular drill bit guide, removing said template and affixing said tibial tray to said tibial horizontal cut surface with said tibial tray mounting peg located in said drilled tibial hole.

14. The method claimed in claim 13 including the step of applying bone adhesive between said tibial tray and said tibial horizontal cut surface.

15. The method claimed in claim 13 including the steps of providing each of said right and left tibial templates with medial and anterior surgical drill bit guide holes, Providing said tibial tray with corresponding medial and anterior perforations, drilling medial and anterior holes in said tibial horizontal cut surface using said medial and anterior drill bit guide holes of said appropriate template, and mounting screws in said tibial tray and horizontal cut surface medial and anterior holes.

16. The method claimed in claim 13 including the step of locating said appropriate tibial template on said tibial plateau after mounting said tibial IM rod with said template arcuate side surface aligned with the medial edge of the tibial cortex, measuring the distance between said rectilinear template side surface and said tibial IM rod, and selecting an appropriately sized vertical tibial cutting block in accordance with said measurement.

17. A method of replacing the articulating femoral surface of a knee joint in which the diseased area is restricted to one of the medial and lateral compartments, said method comprising the steps of measuring the size of the affected condyle, drilling a hole immediately superior to the intercondylar notch, inserting a femoral IM rod in said hole and down the center of the femur, selecting an appropriately sized femoral cutting block having surgical saw blade guide slots for the posterior and distal articular surface cuts and the posterior and anterior chamfer cuts, adjustably bolting one side of said femoral cutting block to the free end of said femoral IM rod, providing a femoral cutting block locating instrument comprising a handle supporting at one end a plate-like member formed into a U-shape having a base portion to which said handle is affixed and a short leg and a long leg in parallel spaced relationship, inserting said short leg of said instrument into the posterior articular surface cut guide slot of said femoral cutting block with said long leg extending rearwardly past the adjacent end of said femoral cutting block, causing said long leg of said instrument to contact the femoral posterior condyle to adjust said femoral cutting block in the anterior-posterior plane, adjustably securing an outrigger plate to the other side of said femoral cutting block, securing the free end of said outrigger plate to the femur with smooth pins, performing all of said femoral cuts in any order, removing said outrigger plate, said femoral cutting block and said femoral IM rod, selecting a conventional femoral prosthesis, and mounting said femoral prosthesis on said femur.

18. A method of replacing the articulating femoral surface of a knee joint in which the diseased area is restricted to one of the medial and lateral compartments, said method comprising the steps of measuring the size of the affected condyle, drilling a hole immediately superior to the intercondylar notch, inserting a femoral IM rod in said hole and down the center of the femur, selecting an appropriately sized femoral cutting block having surgical saw blade guide slots for the posterior and distal articular surface cuts and the posterior and anterior chamfer cuts, adjustably bolting one side of said femoral cutting block to the free end of said femoral IM rod, adjustably securing an outrigger plate to the other side of said femoral cutting block, said outrigger plate having a planar surface facing away from said diseased condyle, affixing a rod-like handle/alignment bar to said outrigger plate extending perpendicularly from said surface thereof, using said handle/alignment bar to adjust the rotational alignment of said femoral cutting block, securing the free end of said outrigger plate to the femur with smooth pins, performing all of said femoral cuts in any order, removing said outrigger plate, said femoral cutting block and said femoral IM rod, selecting a conventional femoral prosthesis, and mounting said femoral prosthesis on said femur.

* * * * *

UNITED STATES PATENT AND TRADEMARK OFFICE
CERTIFICATE OF CORRECTION

PATENT NO. : 5,234,433
DATED : August 10, 1993
INVENTOR(S) : Jack M. Bert & Richard W. Woods It is certified that error appears in the above—identified patent and that said Letters Patent is hereby corrected as shown below:

Column 15, line 6, (Claim 6) "as" should read --a--

Column 15, line 11, (Claim 6) "chamber" should read --chamfer--

Column 15, line 25, (Claim 6) "laterail" should read --lateral--

Column 15, line 39, (Claim 6) "affect" should read --affected--

Column 15, line 6, "this" should read --the--.

Signed and Sealed this

Nineteenth Day of April, 1994

Attest:

BRUCE LEHMAN

Attesting Officer

Commissioner of Patents and Trademarks